(12) United States Patent
McComsey et al.

(10) Patent No.: US 8,084,490 B2
(45) Date of Patent: Dec. 27, 2011

(54) SULFAMATE AND SULFAMIDE DERIVATIVES USEFUL FOR THE TREATMENT OF EPILEPSY AND RELATED DISORDERS

(75) Inventors: David F. McComsey, Warminister, PA (US); Michael H. Parker, Chalfont, PA (US); Allen B. Reitz, Lansdale, PA (US); Bruce E. Maryanoff, Forest Grove, PA (US)

(73) Assignee: Janssen Pharmaceutica N.V. (BE)

( * ) Notice: Subject to any disclaimer, the term of this patent is extended or adjusted under 35 U.S.C. 154(b) by 764 days.

(21) Appl. No.: 11/154,443

(22) Filed: Jun. 16, 2005

(65) Prior Publication Data

US 2006/0041008 A1 Feb. 23, 2006

Related U.S. Application Data

(60) Provisional application No. 60/580,178, filed on Jun. 16, 2004.

(51) Int. Cl.
*A61K 31/357* (2006.01)
*C07D 319/20* (2006.01)

(52) U.S. Cl. ........ 514/452; 514/450; 514/456; 514/465; 549/349; 549/350; 549/359; 549/366; 549/404; 549/433; 549/443

(58) Field of Classification Search .................. 549/349, 549/350, 359, 362, 404, 433, 443; 514/450, 514/452, 456, 465
See application file for complete search history.

(56) References Cited

U.S. PATENT DOCUMENTS

| | | | |
|---|---|---|---|
| 2,527,861 A | 10/1950 | Walter | |
| 3,143,549 A | 8/1964 | Lafferty et al. | |
| 3,318,952 A | 5/1967 | Houlihan | |
| 3,383,414 A | 5/1968 | Houlihan | |
| 3,539,573 A | 11/1970 | Schmutz | |
| 3,621,096 A | 11/1971 | Prange et al. | |
| 4,513,006 A | 4/1985 | Maryanoff et al. | |
| 4,539,413 A | 9/1985 | Mouzin et al. | |
| 4,710,500 A | 12/1987 | Perregaard | |
| 4,804,663 A | 2/1989 | Kennis et al. | |
| 4,831,031 A | 5/1989 | Lowe, III et al. | |
| 4,879,288 A | 11/1989 | Warawa et al. | |
| 5,112,838 A | 5/1992 | Perregaard et al. | |
| 5,158,952 A | 10/1992 | Janssen et al. | |
| 5,192,785 A | 3/1993 | Lo et al. | |
| 5,194,446 A | 3/1993 | Lo et al. | |
| 5,212,326 A | 5/1993 | Meade | |
| 5,229,382 A | 7/1993 | Chakrabarti et al. | |
| 5,238,945 A | 8/1993 | Perregaard et al. | |
| 5,242,942 A | 9/1993 | Costanzo et al. | |
| 5,258,402 A | 11/1993 | Maryanoff | |
| 5,273,993 A | 12/1993 | Lo et al. | |
| 5,312,925 A | 5/1994 | Allen et al. | |
| 5,384,327 A | 1/1995 | Costanzo et al. | |
| 5,387,700 A | 2/1995 | Maryanoff et al. | |
| 5,731,348 A | 3/1998 | Gu et al. | |
| 5,753,693 A | 5/1998 | Shank | |
| 5,753,694 A | 5/1998 | Shank | |
| 5,760,007 A | 6/1998 | Shank et al. | |
| 5,780,650 A | 7/1998 | Furukawa et al. | |
| 5,935,933 A | 8/1999 | Shank et al. | |
| 5,998,380 A | 12/1999 | Ehrenberg et al. | |
| 6,071,537 A | 6/2000 | Shank | |
| 6,150,419 A | 11/2000 | Fairbanks et al. | |
| 6,187,338 B1 | 2/2001 | Caruso et al. | |
| 6,191,163 B1 | 2/2001 | Cottrell | |
| 6,211,241 B1 | 4/2001 | Islam et al. | |
| 6,319,903 B1 | 11/2001 | Carrazana et al. | |
| 6,322,503 B1 | 11/2001 | Sparhawk, Jr. | |
| 6,323,236 B2 | 11/2001 | McElroy | |
| 6,391,877 B1 | 5/2002 | Islam et al. | |
| 6,503,884 B1 | 1/2003 | Ehrenberg et al. | |
| 6,559,293 B1 | 5/2003 | Almarsson et al. | |
| 6,562,865 B1 | 5/2003 | Codd et al. | |
| 6,583,172 B1 | 6/2003 | Shank | |
| 6,627,653 B2 | 9/2003 | Plata-Salaman et al. | |
| 6,852,701 B2 | 2/2005 | Plata-Salaman et al. | |
| 6,852,738 B2 | 2/2005 | Jones et al. | |
| 6,949,518 B1 | 9/2005 | Chu et al. | |
| 2001/0008889 A1 | 7/2001 | Caruso et al. | |
| 2002/0015713 A1 | 2/2002 | Murdock et al. | |
| 2004/0073037 A1 | 4/2004 | Jones | |
| 2004/0192690 A1 | 9/2004 | Buxton et al. | |
| 2004/0253223 A1 | 12/2004 | Rodriguez | |
| 2005/0148603 A1 | 7/2005 | Jimenez et al. | |
| 2005/0282887 A1 | 12/2005 | McComsey et al. | |
| 2006/0047001 A1 | 3/2006 | Parker et al. | |
| 2006/0270856 A1 | 11/2006 | Abdel-Magid et al. | |
| 2006/0276528 A1 | 12/2006 | Abdel-Magid et al. | |
| 2007/0293440 A1 | 12/2007 | Smith-Swintosky et al. | |
| 2007/0293476 A1 | 12/2007 | Smith-Swintosky et al. | |

(Continued)

FOREIGN PATENT DOCUMENTS

CA 2416647 A 1/2003

(Continued)

OTHER PUBLICATIONS

U.S. Appl. No. 11/154,386, McComsey David F.
U.S. Appl. No. 11/209,122, Maryanoff Bruce E.
U.S. Appl. No. 11/611,938, Smith-Swintosky.
U.S. Appl. No. 11/611,961, Reitz Allen B.
U.S. Appl. No. 11/612,071, Reitz Allen B.
U.S. Appl. No. 11/612,146, Reitz Allen B.
U.S. Appl. No. 11/612,174, Smith-Swintosky.
U.S. Appl. No. 11/612,202, Reitz Allen B.
U.S. Appl. No. 11/612,222, Reitz Allen B.
U.S. Appl. No. 11/612,249, Reitz Allen B.
U.S. Appl. No. 11/673,705, Smith-Swintosky.
U.S. Appl. No. 11/673,709, Smith-Swintosky.

(Continued)

*Primary Examiner* — Bernard Dentz
(74) *Attorney, Agent, or Firm* — Hal B. Woodrow

(57) ABSTRACT

The present invention is directed to novel sulfamide and sulfamate derivatives, pharmaceutical compositions containing them and their use in the treatment of epilepsy and related disorders.

20 Claims, No Drawings

U.S. PATENT DOCUMENTS

| | | | |
|---|---|---|---|
| 2009/0182141 A1 | 7/2009 | Abdel-Magid et al. |
| 2009/0247617 A1 | 10/2009 | Abdel-Magid et al. |
| 2009/0247618 A1 | 10/2009 | Ballentine et al. |
| 2009/0318544 A1 | 12/2009 | Mehrman et al. |

FOREIGN PATENT DOCUMENTS

| | | | |
|---|---|---|---|
| DE | 2022370 | | 12/1971 |
| DE | 1211166 | | 2/1996 |
| DK | 9800727 | A | 5/1998 |
| EP | 0138441 | B1 | 4/1985 |
| EP | 0483881 | B1 | 5/1992 |
| EP | 490689 | | 6/1992 |
| EP | 498770 | | 8/1992 |
| EP | 503440 | A1 | 9/1992 |
| EP | 0478954 | | 10/2000 |
| EP | 1056733 | | 12/2000 |
| EP | 1118610 | | 7/2001 |
| GB | 1087602 | | 10/1967 |
| GB | 1111706 | | 5/1968 |
| RU | 2226357 | | 4/2004 |
| RU | 2246727 | | 8/2004 |
| WO | 94/14827 | A1 | 7/1994 |
| WO | 95/17406 | A1 | 6/1995 |
| WO | 96/06822 | A1 | 3/1996 |
| WO | 97/13510 | A1 | 4/1997 |
| WO | 97/19919 | | 6/1997 |
| WO | WO 97/19682 | A1 | 6/1997 |
| WO | 97/35584 | A1 | 10/1997 |
| WO | 98/00123 | | 1/1998 |
| WO | 98/00124 | A1 | 1/1998 |
| WO | 98/00130 | A2 | 1/1998 |
| WO | 98/00131 | A1 | 1/1998 |
| WO | 98/06708 | A1 | 2/1998 |
| WO | 98/07447 | A1 | 2/1998 |
| WO | 98/15270 | | 4/1998 |
| WO | 99/44581 | A2 | 9/1999 |
| WO | 99/62522 | A2 | 12/1999 |
| WO | 00/01376 | A2 | 1/2000 |
| WO | 00/07583 | A2 | 2/2000 |
| WO | 00/042995 | A2 | 7/2000 |
| WO | 00/042996 | A2 | 7/2000 |
| WO | 00/49017 | | 8/2000 |
| WO | 00/50020 | A2 | 8/2000 |
| WO | 00/54588 | A1 | 9/2000 |
| WO | 00/61137 | | 10/2000 |
| WO | 00/61139 | A1 | 10/2000 |
| WO | 00/61140 | A1 | 10/2000 |
| WO | 00/66109 | A2 | 11/2000 |
| WO | 00/76493 | A1 | 12/2000 |
| WO | 01/13904 | A2 | 3/2001 |
| WO | 01/76576 | A2 | 10/2001 |
| WO | 02/03984 | | 1/2002 |
| WO | 02/07821 | | 1/2002 |
| WO | 02/09694 | | 2/2002 |
| WO | 02/30881 | | 4/2002 |
| WO | 02/089785 | | 11/2002 |
| WO | WO 02/096424 | A1 | 12/2002 |
| WO | 2004/014352 | | 2/2004 |
| WO | WO 2004/093912 | A1 | 4/2004 |
| WO | WO 2004/092216 | A1 | 10/2004 |
| WO | WO 2004/096771 | A1 | 11/2004 |
| WO | WO 2004/098584 | A1 | 11/2004 |
| WO | WO 2005/020917 | A2 | 3/2005 |
| WO | 2006/007435 | | 1/2006 |
| WO | 2006/007436 | | 1/2006 |
| WO | WO 2006/010008 | A1 | 1/2006 |
| WO | WO 2006/010750 | A1 | 2/2006 |
| WO | WO 2006/023861 | A1 | 3/2006 |
| WO | 2006/127184 | | 11/2006 |
| WO | 2007/075695 | | 7/2007 |
| WO | 2007/075698 | | 7/2007 |
| WO | 2007/075717 | | 7/2007 |
| WO | 2007/075751 | | 7/2007 |
| WO | 2007/075752 | | 7/2007 |
| WO | 2007/075833 | | 7/2007 |
| WO | 2007/075834 | | 7/2007 |
| WO | 2007/092086 | | 8/2007 |
| WO | 2007/095615 | | 8/2007 |
| WO | 2007/095618 | | 8/2007 |
| WO | 2007/098486 | | 8/2007 |
| WO | 2007/137167 | | 11/2007 |
| WO | 2009/089210 | | 7/2009 |
| WO | 2009/120191 | | 10/2009 |
| WO | 2009/120192 | | 10/2009 |

OTHER PUBLICATIONS

U.S. Appl. No. 11/673,713, Smith-Swintosky.
U.S. Appl. No. 11/673,723, Smith-Swintosky.
PCT International Search Report, PCT/US2005/029814, Nov. 9, 2005, U.S. Appl. No. 11/209,122.
PCT International Search Report, PCT/US2005/021513, Sep. 27, 2005, U.S. Appl. No. 11/154,443.
PCT International Search Report, PCT/US2005/021515, Jun. 16, 2005; U.S. Appl. No. 11/154,386.
U.S. Appl. No. 11/673,977, Smith-Swintosky.
U.S. Appl. No. 11/673,987, Smith-Swintosky.
U.S. Appl. No. 11/673,998, Smith-Swintosky.
U.S. Appl. No. 11/674,011, Smith-Swintosky.
U.S. Appl. No. 11/674,021, Smith-Swintosky.
U.S. Appl. No. 11/677,717, Fawzy Nagy.
U.S. Appl. No. 60/883,442, Smith-Swintosky.
Ca 835894-69-4 Sulfamide (1,3-benzodioxol-2-ylmethyl).
CA PLUS 835894-67-2 Sulfamic acid (1,3-benzodioxol-2-ylmethyl ester).
CA PLUS 835894-65-0 Sulfamide [(3, 4-dihydro-2H-1-benzopyran-2-yl) methyl].
CA PLUS 835894-63-8 Sulfamic acid (3,4-dihydro-2H-1-benzopyran-2-yl)methyl ester.
Maryanoff et al.: Anticonvulsant O-Alkyl Sulfamates 2,3:4,5-Bis-O-(1-methylethylidene)-betas-D-fructopyranose Sulfamate and Related Compounds, J.Med. Chem., vol. 30, No. 5, 1987, pp. 880-887.
Maryanoff et al.: "Comparison of Sulfamates and Sulfamide Groups for the Inhibition of Carbonci Anhydrase-II by Using Topiratmate as a Structural Platform", J. Med. Chem, vol. 48, No. 6, 2004, pp. 1941-1947.
Levy RH et al., eds. Antiepileptic Drugs. $3^{rd}$ ed. New York: Raven Press, 1989:85-102.
Office Action mailed Jan. 29, 2009 in U.S. Appl. No. 11/612,174.
Office Action mailed Nov. 26, 2008 in U.S. Appl. No. 11/612,071.
Office Action mailed May 2, 2008 in U.S. Appl. No. 11/611,961.
Final Office Action mailed Jan. 29, 2009 in U.S. Appl. No. 11/611,961.
Office Action mailed May 21, 2008 in U.S. Appl. No. 11/674,021.
Office Action mailed Aug. 5, 2008 in U.S. Appl. No. 11/612,146.
Office Action mailed Oct. 3, 2007 in U.S. Appl. No. 11/154,386.
Office Action mailed Jul. 9, 2009 in U.S. Appl. No. 11/154,386.
Notice of Allowance dated Mar. 6, 2009 in U.S. Appl. No. 11/154,386.
Office Action mailed Apr. 14, 2008 in U.S. Appl. No. 11/209,122.
Notice of Allowance dated Oct. 30, 2008 in U.S. Appl. No. 11/209,122.
Office Action mailed Mar. 20, 2009 in U.S. Appl. No. 11/209,122.
BESAG FMC: "Behavioural Effects of the New Anticonvulsants" Drug Safety, Adis Press, Auckland, NZ, vol. 24, No. 7, 2001, pp. 513-536.
Guillaume et al., "Glial contribution to seizure: Carbonic anhydrase activity in epileptic mammalian brain" Epilepsia, 1991, vol. 32, No. 1, 1991, pp. 10-15.
Johnson, B., "Progress in the development of topiramate for treating alcohol dependence: From a hypothesis to a proof-of-concept study" Alcoholism: Clinical and Experimental Research, vol. 28, No. 8, 2004, pp. 1137-1144.
Klinger et al., "Inhibition of carbonic anhydrase-II by sulfamate and sulfamide groups: An investigation involving direct thermodynamic binding measurements" Journal of Medicinal Chemistry, vol. 49, No. 12, Jun. 15, 2006, pp. 3496-3500.
Mula et al., "The role of anticonvulsant drugs in anxiety disorders: a critical review of the eVidence" Journal of Clinical Psychopharmacology, Williams and Wilkins, vo 1.27, No. 3, 2007, pp. 263-272.

Nies et al., Goodman & Gilman's The Pharmacological Basis of Therapeutics, 9th Edition, pp. 43-62, 1996.
Raguraman, et al., "Effects of topiramate in alcohol dependence [2]" Australian and New Zealand Journal of Psychiatry, vol. 39, No. 8, 2005, pp. 736-737.
Scozzafava A et al: "Modulation of carbonic anhydrase activity and its applications in therapy" Expert Opinion on Therapeutic Patents, vol. 14, No. 5, 2004, pp. 667-702.
Shank et al., "Examination of two independent kinetic assays for determining the inhibition of carbonic anhydrases I and II: Structure-activity comparison of sulfamates and sulfamides" Chemical Biology and Drug Design, vol. 68, No. 2, 2006, pp. 113-119.
Tenovuo, O., "Central acetylcholinesterase inhibitors in the treatment of chronic traumatic brain injury—Clinical experience in 111 patients" Progress in Neuro-Psychopharmacology and Biological Psychiatry, 2005, vol. 29, No. 1, Jan. 2005, pp. 61-67.
Waugh et al., "Topiramate: As Monotherapy in Newly Diagnosed Epilepsy" CNS Drugs, vol. 17, No. 13, 2003, pp. 985-992.
U.S. Appl. No. 12/502,472, filed Jul. 14, 2009, McComsey et al.
Aeberli, P. et al. "Neuropharmacological Investigation of N-Benzylsulfamides", Journal of Medicinal Chemistry, Jul. 1967, vol. 10, No. 4, pp. 636-642.
Drach et al. N-1,2,2,2-tetrachloroethyl-N, N-dimethylsulphamide, Journal of organic chemistry of the USSR, v. 13, N. 7, 1977, p. 1289-1294.
Huisman et al: Synthesis of N-(diemthylsulphamoyl)aldimines, a new type of aldimine derivative, Synthetic Communications, v. 27, N. 6, 1997, p. 945-952.
Kohno et al., A novel synthesis of isoquinolines containing an electron withdrawing substituent, Heterocycles, v. 51, N. 1, 1999.
Maryanoff et al., Structure-activity studies on anticonvulsant sugar sulphmates related to topirmate. Enhanced potency with cyclic sulphate derivatives, J.Med.Chem, 1998, v. 41, N. 8, p. 1315-1343.
Pansare et al., Intramolecular imine cross-coupling in dibenzylidine sulphamides: synthesis of unsymmetrical 1,2-diaryl ethanediamines, Tetrahedron Letters, v. 37, N. 16, p. 2859-2862.
ten Have, et al., Tetrahedron, 1997, 53(33), 11355-11368.
Traube et al., Zur Kenntnis des Sulfamids, Berichte Der Deutschen Chemischen Gesellschaft, v. 56, 1923, p. 1656-1663.
Vandi et al., Synthesis and properties of some N-substituted sulphamides, J.Org.Chem., v. 26, n. 4, 1961.
Weib, et al., Uebigs Annalen der Chemie, 1969, 729,40-51.
Whitehead et al., Diuretics.II. Alkoxymercuration oby mixed anion salts of mercury, Journal of the American Chemical Society, v. 80, N. 9, p. 2182-2185.
Ziegler et al., Zur Reaktivitat von C=N-Doppelbindungssystemen, VI. Reaktionen mit Sulfonamiden and Sulfamiden, Zeitscherift Fur Naturforschung, v. 30b, 1975, p. 951-953.
Notice of Allowance dated Sep. 10, 2009 in U.S. Appl. No. 11/154,386.
Notice of Allowance dated Feb. 23, 2010 in U.S. Appl. No. 11/154,386.
Notice of Allowance dated Sep. 24, 2009 in U.S. Appl. No. 11/209,122.
Notice of Allowance dated Jan. 13, 2010 in U.S. Appl. No. 11/209,122.
Notice of Allowance dated Mar. 13, 2009 in U.S. Appl. No. 11/406,794.
Notice of Allowance dated Jul. 17, 2009 in U.S. Appl. No. 11/406,794.
Notice of Allowance dated Mar. 17, 2010 in U.S. Appl. No. 11/406,794.
Notice of Allowance dated Jun. 2, 2009 in U.S. Appl. No. 11/611,961.
Notice of Allowance dated Jan. 6, 2010 in U.S. Appl. No. 11/611,961.
Notice of Allowance dated Apr. 30, 2010 in U.S. Appl. No. 11/611,961.
Alcaraz et al., Org. Lett., 2004, 6(16), pp. 2705-2708.
Beaudoin et al., J. Org. Chem., 2003, 68, pp. 115-119.
Birch et al., J. Med. Chem., 1999, 42, pp. 3342-3355.
Delgado et al., Tet Lett, 1988, 29(3), pp. 3671-3676.
Estave et al., Tet Lett, 2002, 43, pp. 1019-1021.
Gavernet et al., Bioorg & Med Chem., 2007, 15, pp. 5604-4516.
Hedayatullah et al., Phosphorus and Sulfur, 1985, 25(1), pp. 33-38.
Hirayama et al., Bioorg & Med Chem., 2002, 10, pp. 1509-1523.
Kim et al., Tet Lett, 23(14), pp. 1505-1508.
Kubicki et al., J Mol Struct., 2001, 531(1-3), p. 65-70.
Lee et al., Org. Chem 1990 55(25) pp. 6098-6104.
Muniz et al., Synlett, 2005, 1, pp. 149-151.
Nelson et al., J. Med. Chem., 1977, 20(7), pp. 880-885.
Nelson et al., J. Med. Chem., 1979, 22(9), pp. 1125-1127.
Nicolaou et al., Chem. Eur. J., 2004, 10, pp. 5581-5606.
Okada et al., Tet Lett, 2000, 41, pp. 7047-7051.
Park et al., J. Med. Chem., 2002, 45, pp. 5295-5302.
Winum et al., Org. Lett., 2001, 3(14), pp. 2241-2243.
Xu et al., Synlett, 2004, 11, pp. 1901-1904.
Zhong et al., J. Comb. Chem., 2004, 6, pp. 556-563.
Ambrosini, P.J., Psychiatr. Serv. 2000, 51, 627-633.
American Diabetes Association, "Definition and Description of Diabetes Mellitus", Diabetes Care, Jan. 2006; p. S43-S48, vol. 29 Supplement 1.
Ananth, J., Psychother. Psychosom. 1998, 67, 61-70.
Angehagen, Mikael et al., "Does topiramate (TPM) have protective effects on astroglia cells and neurons in primary cortical cultures", Epilepsia, (1998) vol. 39, No. Suppl 6, pp. 44, XP000923162 abstract 2.050.
Ayata et al., "Suppression of cortical Spreading Depression in Migraine Prophylaxis", Ann Neurol 2006; 59:652-661.
Barry et al. Current status of the utilization of antiepileptic treatmetns in mood, anxiety and aggression: drugs and devices, Jan. 2004, 35, 1.
Beck-Nielsen H., "In Vivo Glucose Metabolism, Insulin Secretion and, Insulin Action in Europids with Non-insulin-dependent Diabetes Mellitus (NIDDM) and Their First-degree Relatives", Diabet Med Sep. 1996;13(9 Suppl 6):578-84.
Berman, R.M. et al., Depress. Anxiety 1997, 5, 154-164.
Breslau et al., "The impact of migraine. Epidemiology, risk factors, and comorbidities" Neurology, 2001;56:54-S12 (Abstract only).
Burton et al. Anti-epileptic drugs for pain management. Pain, Symptom, Control and Palliative Care, 2001, vol. 1, No. 2.
Cadieux, R.J., Am. Fam. Physician 1998, 58, 2059-2062.
Calabrese, J.R. et al., Eur. Neuropsychopharmacol. 1999, 9, S109-S112.
Calabresi et al., "Antiepileptic drugs in migraine: from clinical aspects to cellular mechanisms", TRENDS in Pharmacological Sciences, vol. 28, No. 4, 188-195 (2007).
Caumo A., "Insulin Sensitivity from Meal Tolerance Tests in Normal Subjects: A Minimal Model Index", J Clin Endocrinol Metab, 85(11):4396-402 2000.
Cavaletti G et al: "Experimental peripheral neuropathy induced in adult rats by repeated intraperitoneal administration of Taxal", Exper Neurol 133:64-72, 1995.
Chaplan Sr et al: "Quantitative assessment of tactile allodynia in the rat paw". J Neurosci Meth, 53:55-63, 1994.
Crooke et al, Abstract, Topiramate Improves Glycemic Control Independent of Weight Loss in ob/ob Mice.diabetes. A Journal of the American Diabetes Association, Abstract Book 61st Scientific Sessions Friday, Jun. 22-Tuesday Jun. 26, 2001, 2158-PO, A513.
Demarest et al, Abstract, Topiramate Improves Glucose Tolerance and May Improve Insulin Sensitivity in Animal Models of Type 2 Diabetes Mellitus, diabetes, A Journal of the American Diabetes Association, Abstract Book 61st Scientific Sessions Friday, Jun. 22-Tuesday Jun. 26, 2001, 1254-P, A302.
Diamond et al, "Practical Approaches to Migraine Management", 2002, CNS Drugs, 16(6), pp. 385-403.
Dickenson et al. Neurobiology of neuropathic pain: mode of action of anticonvulsants. European Journal of Pain, 2002, 6 (Suppl. A): 51-60, 2002.
Dinneen S.F., "The Postprandial State: Mechanism of Glucose Intolerance", Diabet Med Aug. 1997;14 Suppl 3:S19-24.
Dressler et al., Benzodiazepine in geriatric patients . . . , Abstract, Anaesthesiologie and reanimation, 1996, vol. 21/5, pp. 136-138.
Drug Facts and Comparison (1995 Edition, pp. 1607).
Dursun, S.M. et al., "Accelerated weight loss after treating refractory depression with fluoxetine plus topiramate: possible mechanisms of action?", The Canadian Journal of Psychiatry, vol. 46, No. 3, pp. 287-288, 2001.

Edwards, K.R. et al, Efficacy and safety of topiramate in the treatment of painful diabetic neuropathy: a double-blind placebo-controlled study ADIS Title: Topiramate: therapeutic use: Neurogenic pain; In patients with diabetic neuropathy: Neurology 54 (Suppl. 3): 81 Apr. 11, 2000.

Edwards, KR; Glantz, MJ; Button, J et al, Evaluation of Topiramate in The Management of Painful Diabetic Neuropathy. Presented at: 18th Annual Meeting of the American Pain Society; 1998, Fort Lauderdale, FL.

Emancipator K., "Laboratory Diagnosis and Monitoring of Diabetes Mellitus", Am J Clin Pathol, 112(5):665-74 1999.

Erfurth, Andreas et al., "Bupropion as add-on strategy in difficult-to-treat bipolar depressive patients", Neuropsychobiology, vol. 45, No. Sup 1, pp. 33-36, 2002.

Fakhoury et al., Epilepsy Behay. Aug. 2007, abstract.

Flatters, SJL et al: "Acetyl-L-carnitine prevents and reduces paclitaxel-induced painful peripheralneuropathy", Neurosci Lett 397:219-223, 2006.

Gareri, P. et al, Progress in Neurobiology 61, 2000, 353-396.

Garonna, F. et al., "Topiramate in the treatment of overweight/obese binge eaters ADIS Title: Topiramate: therapeutic use; Obseity; In patient with binge eating disorders" International Journal of Neuropsychopharmacology 3(Suppl 1): 299: Jul. 2000 XP001030426 Bassano dG Vicenza Italy, whole document.

Ghaemi et al., Soc. of Bio. Psychiatry, (1999) vol. 45, 137-144.

Goldberg R.G., "Prevention of Type 2 Diabetes", Med Clin North Am, Jul. 1998;82(4):805-21.

Gorelick D a, "Pharmacological treatment" Recent Developments in Alcoholism, vol. 11, 1993, p. 413-427, XP00913482 p. 417.

Gorelick et al., Drugs 2004: 64(14), pp. 1547-1573.

Grond et al., "Weak Opiods—an educational substitute for morphine?", Current Opinion in Anaesthesiology, vol. 11, No. 5, 1998, pp. 559-565 XP00982759.

Groop L., "Characterization of the Prediabetic State", Am J Hypertension; Sep. 1997;10(9 Pt 2):1725-180S.

Haffner S.M., "Impaired Glucose Tolerance, Insulin Resistance and Cardiovascular Disease", Diabetic Medicine, Aug. 1977;14 Suppl 3:S12-8.

Haffner S.M., "The Prediabetic Problem: Development of Non-Insulin-Dependent Diabetes Mellitus and Related Abnormalities", J Diabetes Complications, Mar.-Apr. 1997; 11(2):69-76.

Harrison's Principles of Internal Medicine, Isselbacher et al. eds. McGraw-Hill, Inc., New York, 1994, p. 69.

Harrison'S Principles of Internal Medicine, vol. 2, 23d ed., Ed by Isselbacher, Braunwald, Wilson, Martin, Fauci and Kasper, McGraw-Hill Inc New York City, 1994, p. 2275.

Hatzinger, M. et al., Wien. Med. Wochenschr. 1999, 149, 511-514.

Hauner H, "Managing type 2 diabetes mellitus in patients with obesity," Treatments in Endocrinology, 2004, 3(4), 223-232 (only abstract provided).

Headache Classification Committee of the International Headache Society. Cephalalgia 1988;8 Suppl 7:1-96.

Hering et al., "Sodium valproate in the treatment of cluster headache", Cephalalgia (Sep. 1989) 9(3) pp. 195-198.

Jay et al., "Epilepsy, Migraine and EEG Abnormalities in Children: a Review & Hypothesis," Journal of Head and Face Pain, abstract, vol. 22, Issue 3, pp. 110114, 1982.

Joffe, R.T. et al., Arch. Gen. Psychiatry 1993, 50, 397-393.

Johns Hopkins Clinical Trial of Topiramate for Cocaine Addiction (ClinicalTrials.gov).

Johnson, SA CNS Drugs, 2005. vol. 19, No. 1 0, pp. 873-896.

Kawasaki, "Structural and functional analysis of pancreatic islets preserved by pioglitazone in db/db mice", Am J Physiol Endocrinol Metab; 2004, p. E510-E518, doi 10.1152/ajpendo.00128.2004.

Keck, P et al, "Valproate and carbamazepine in the treatment of panic and post traumatic stress disorders, withdrawals states . . . " J Clin Psychopharm, vol. 12, No. 1, p. 36S-41S, (1992).

Kent, J.M., Lancet 2000, 355, 911-918.

Ketter, T.A. et al., J. Clin. Psychiatry 1995, 56, 471-475.

Keung W.M. et al, "Daidzin and daidzein suppress free-choice ethanol intake by Syrian golden hamsters" Proc Natl Acad Sci, vol. 90, p. 1008-10012, Nov. 1993.

Kralinsky E.A. Tramal in the treatment of pain in children with malignancies XP002162259 English Abstract & Klinicka Onkologie, vol. 7, No. 6, 1994, pp. 182185.

Kunkler et al., "Hippocampal Spreading Depression Bilaterally Activates the Caudal Trigeminal Nucleus in Roadent", Hippocampus 13:835-844 (2003).

Kuzniecky et al., "Topiramate increases cerebral GABA in healthy humans", Neurology (Aug. 1998) 51(2) pp. 627-629.

Kyowa Hakko, "Topiramate" Drugs of the Future, ES, Barcelona, vol. 21, No. 4, Jan. 1, 1996; p. 463-465, XP002043895.

Langtry H.D. et al, "Topiramate, A review of its pharmacodynamic and pharmacokinetic properties and clinical efficacy in the management of epilepsy" Drugs, (1997) 54/5 pp. 752-773, XP002179441.

Lydiard, R.B. et al., J. Clin. Psychiatry 1998, 59, Suppl. 18, 10-17.

Malatynska et al., "Dominant-submissive behavior as models of mania and depression", Neuroscience and Biobehavioral Review, 29 (2005) 715-737.

Malatynska et al., "Submissive behavior in mice as a test for antidepressant drug activity", Neuroscience and Biobehavioral Review, 82 (2005) 306-313.

Mathew, Ninan T., MD, et al, "Prophylaxis of Migraine, Transformed Migraine, and Cluster Headache with Topiramate" Headache (2002), (42)796-803.

Mathew, N. T. "Antiepileptic Drugs in Migraine Prevention", 2001, Headache, Nov./Dec. Suppl 2001, pp. S18-S24.

Mazzotta et al., J Headache Pain, 2004 5:S67-S70.

McElroy, S.L. et al., "A pilot trial of adjunctive topiramate in the treatment of bipolar disorder ADIS Title: Topiramate: therapeutic use; Bipolar disorder: A pilot trial of adjunctive treatment" retrieved from STN Database Accession No. 1998:39968 XP00217779443 Abstract & XXIST CINP Congress (Jul. 12, 1998) pp. 281 (Poster) University of Cincinnati College of Medicine, Cincinnati, OH.

Meldrum B. et al., "Excitatory amino acid neurotoxicity and neurodegenerative disease" TIPS, vol. 11, 1990, pp. 379-387, XP000915223.

Migraine: Treatments and drugs, by Mayo Clinic Staff, http://www.mayoclinic.com/health/migraineheadache/DS00120/DSECTION=treatments-and-drugs, (2009).

Mueller T I, "A double-blind, placebo-controlled pilot study of carbamazepine for the treatment of alcohol dependence", Alcoholism Clin Exp Res, vol. 21, No. 1, 1997, p. 86-92, X00913485.

Moller, H.J. et al., Eur. Arch. Psychiatry Clin. Neurosci. 2000, 250, 57-68.

Moskowitz, M.A., "The Neurobiology of Vascular Head Pain", Annals of Neurology, vol. 16, Issue 2, pp. 157-168, 1984.

Myers, R.D., "New Drugs for the Treatment of Experimental Alcoholism", Alcohol, vol. 11, No. 6, 1994, p. 439-451.

Nemeroff, C.B., Depress. Anxiety 1996-1997, 4, 169-181.

Nickel et al., Journal of Affective Disorders, vol. 87(2-3), 2005, pp. 243-252.

Olesen et al., "Spreading Cerebral Oligiemia in Classical- and Normal Cerebral Blood Flow in Common Migraine", Department of Neuromedicine, Rigshospitalet 2100 Copenhagen, Denmark, Jan. 28, 1982 (Headache 22:242-248, 1982).

Olson et al [Editors]. Remington's Pharmaceutical Sciences, pp. 420-425, 1980.

Osborne et al, Abstract, Topiramate Improves Glycemic Control and Triglycerides in Animal Models 1 p. The Posters were presented at the American Diabetes Association Conference held Jun. 22-26 in Philadelphia, diabetes, A Journal of the American Diabetes Association, Abstract Book 61st Scientific Sessions Friday, Jun. 22-Tuesday Jun. 26, 2001, 1255-P, A302.

Ottman et al., "Comorbidity of migraine and epilepsy", Neurology, 1994;44: 2105 (Abstract only).

Pascual D et al: "A cannabinoid agonist, WIN55,212-2, reduces neuropathic nocicipetion induced by paclitaxel in rats" Pain 118:23-34, 2005.

Penovich et al., "Weight Loss in Patients Receiving Topiramate for Intractable Epilepsy", 1994, Neurology 44 (Suppl. 2) Abstract 309P, 46th Annual Meeting of the American Academy of Neurology, Washington, D.C.

Perry et al. "Sumatriptan: An Updated Review of its Use in Migraine", 1998, Drugs, vol. 55, No. 6, pp. 889-922.

Pini et al., "Anti-Epileptic Drugs in the Preventive Treatment of Migraine Headache: a Brief Review", (J. Headache Pain, 2001, 2:13-19.
Polomano et al: "A painful peripheral neuropathy in the rat produced by the chemotherapeutic drug, paclitaxel", Pain, 94:293-304, 2001.
Prado Lima, P.A.S. et al., "Topiramate in treatment-refractory depression" retrieved from STN Database accession No. 1999:61852 XP002179442 Abstract & 11$^{th}$ World Congress of Psychiatry (Aug. 6, 1999), vol. 2,00.126.
Ramlo-Halsted BA, "The Natural History of Type 2 Diabetes", Primary Care Dec. 1999;26(4):771-89.
Reis et al. Craving decrease with topiramate in outpatient treatment for cocaine dependence: an open label trial, Rev Bras Psiquiatr 2008;30(2):132-5.
Rogaswki et al., Nature Medicine, vol. 10, No. 7, Jul. 2004, pp. 685-692.
Rogawski et al., Nature Reviews Neuroscience, vol. 5 (1), 2004, pp. 553-564.
Rost et al., The effect of tramadol and other analgesics on the pain . . . , Abstract, Arzneim-Forsch. 1978, vol. 28 (1a0 pp . . . 181-183).
Rouillon, F., Eur. Neuropsychopharmacol 1999, 9 Suppl. 3, S87-S92.
Rygula et al., "Anhedonia and motivational deficits in rats: Impact of chronic social stress", Behavioral Brain Research, 162 (2005) 127-134.
Sanacora, G. et al., "Impairment of GAB Aergic transmission in depression: New Insights from neuroimaging studies", Critical Reviews in Neurobiology, (2000) 14/1 pp. 23-45, XP001029967, whole document.
Sharma K, McCue P, Dunn Sr. Am J Physiol Renal Physiol. Jun. 2003;284(6):F1138-44.
Silberstein et al., "Migraine & Epilepsy", www.myepilepsy.com, 2002.
Sofuoglu et al., CNS Drugs 2005: 19(1), pp. 13-25.
Soledade et al.:"Toward the control of Leptosphaeria Maculans" Design, Synthesis, biological activity, and metabolism of potential detoxification inhibitors of the crucifer phytoalexin brassinin. Bioorganic & Medicinal Chemistry, vol. 14, No. 14, Apr. 17, 2006, pp. 4958-4979, XP005458688.
Stephen, Linda J. et al., "Lamotrigine and topiramate may be a useful combination", The Lancet, vol. 351, No. 9107, pp. 958-959, 1998.
Stephen, Linda J. et al., "Topiramate in Refractory Epilepsy: A Prospective Observational Study", Epilepsia, vol. 41, No. 8, pp. 977-980, 2000.
Stoll et al., Harvard Rev. Psychiatry, Jul./Aug. (1996), vol. 4, No. 2, 77-89.
Storey et al, "Topiramate in Migraine Prevention: A Double Blind, Placebo-Controlled Study", 2001, Headache, 41, pp. 968-975.
The Merck Manual, 1999, Merck Research, Whitehouse Station, NJ XP002224345, Diabetes Mellitus, pp. 165-177.
The Merck Manual (1987), Merck Sharp & Dohme Research Laboratories, Rahway, NJ XP002144176, pp. 1351-1356.
Topiramate retrieved from STN Database Accession No. 1998:2562 XP002179444 Abstract & R&D Focus Drug News, Jul. 27, 1998.
Uhart et al., Addiction Biology, 14, pp. 43-64 (2008).
Uys et al., CNS Neurol Disord Drug Targets, 7(5), 2008, pp. 482-491.
Van Amerigen et al. Antiepileptic drugs in the treatment of anxiety disorders: Role in Therapy, Drugs, 2004, 64(19), 2199-2220.
Seggern, Randal L., et al, "Efficacy of Topiramate in Migraine Prophylaxis: A Retrospective Chart Analysis" Headache (2002), (42)804-809.
Wauquier A et al, "Topiramate: A potent anticonvulsant I the Amygdala-Kindled Rat" Epilepsy Research, NJ, Elsevier Science Publishers, Amsterdam, vol. 24, No. 2, Jun. 1, 1996, p. 73-77, XP002042953.
WebMD Medical News Epilepsy Drugs Fights Migraine, 2002, www.webmd.com/migraine-headaches/news/20020923/epilepsydrug-fights-migraine.
Wheeler et al., "Topiramate-treated cluster headache", Neurology (Jul. 1999) vol. 53, No. 1 pp. 234-236.
Wheeler S.D., "Antiepileptic Drug therapy in Migraine Headache", Current Treatment Options Neurology, Sep. 2002; 4(5):383-394.
Wheeler, "Significance of migrainouse features in cluster headache", Headache (1998) 38/7 pp. 547-551.
Williams, Jr., J.W., et al., Ann. Intern. Med. 2000, 132, 743-756.
Winhusen et al. Drug and Alcohol Dependence 91 (207) 131-148, (2007).
Yang Y. et al., "Neuroprotection by delayed administration of topiratmate in rat model of middle cerebral artery embolization", Brain Research, vol. 804, No. 2, 1998, pp. 169-176, XP000921218.
York, DA et al, "Effects of Topirament on High Fat Diet-Induced Obesity", FASEB journal, Fed. Of America Soc. For Experimental Biology, Bethesda, MD, US., vol. 14, No. 4, Apr. 2000. p. A431, XP000915192.
Young, Wb et al, "Topiramate: a case series study in migraine prophylaxis" Cephalalgia (2002), (22)659-663.
Chemische Berichte, 1959, 92, pp. 509-513.
Agrawal et al., Bioorganic and Medicinal Chemistry, 11(2003), pp. 5353-5362.
Casini et al., Bioorganic and Medicinal Chemistry Letters, 13(2003), pp. 841-845.
Pasorekova et al., Journal of Enzyme Inhibition and Medicinal Chemistry, Jun. 2004, vol. 19(3), pp. 199-229.
Supuran et al., Curr. Med. Chem.—Cardiovascular and Hematological Agents, 2004, 2, pp. 49-68.
Supuran et al., Curr. Med. Chem.—Imm., Endoc. & Metab Agents, 2001, 1, 61-97.
Supuran et al., Exp. Opin. Ther. Patents, (2000), 10(5), pp. 575-600.
Supuran et al., Exp. Opin. Ther. Patents, 12(2), pp. 217-242 (2002).
Supuran et al., Medicinal Research Reviews, vol. 23, No. 2, pp. 146-189, 2003.
Thakur at al., Bioorganic and Medicinal Chemistry, 12(2004), pp. 789-793.
Behl et al., Endocrinology, vol. 138, No. 1, pp. 101-106, (1997).
Coyle et al., Science, vol. 262, Issue 5134, pp. 689-695, (1993).
Desagher et al., The Journal of Neuroscience, 1996, 16(8), pp. 2553-2562.
Tabner et al., The Journal of Biological Chemistry, vol. 280, No. 43, pp. 35789-35792, Oct. 28, 2005.
Taylor et al., Science, vol. 296, pp. 1991-1995 (2002).
Notice of Allowance dated Jul. 1, 2010 in U.S. Appl. No. 11/406,794.
Office Action mailed Sep. 10, 2008 in U.S. Appl. No. 11/406,794.
Office Action mailed Nov. 2, 2009 in U.S. Appl. No. 11/406,794.
Final Office Action mailed Feb. 25, 2010 in U.S. Appl. No. 11/611,938.
Office Action mailed Aug. 17, 2009 in U.S. Appl. No. 11/611,938.
Final Office Action mailed Jun. 8, 2009 in U.S. Appl. No. 11/612,071.
Final Office Action mailed Oct. 29, 2009 in U.S. Appl. No. 11/612,146.
Office Action mailed Mar. 30, 2009 in U.S. Appl. No. 11/612,202.
Office Action mailed Jan. 14, 2010 in U.S. Appl. No. 11/612,202.
Notice of Allowance mailed Jul. 29, 2010 in U.S. Appl. No. 11/612,202.
Office Action dated Jul. 9, 2010 in U.S. Appl. No. 11/612,222.
Final Office Action mailed Jan. 28, 2010 in U.S. Appl. No. 11/612,249.
Office Action mailed Jul. 21, 2009 in U.S. Appl. No. 11/612,249.
Final Office Action mailed Jul. 31, 2009 in U.S. Appl. No. 11/674,021.
Notice of Allowance mailed Jun. 16, 2010 in U.S. Appl. No. 11/674,021.
Office Action mailed Apr. 29, 2009 in U.S. Appl. No. 11/750,600.
Final Office Action mailed Dec. 16, 2009 in U.S. Appl. No. 11/750,600.
Final Office Action mailed Mar. 11, 2010 in U.S. Appl. No. 11/750,600.
Notice of Allowance mailed May 28, 2010 in U.S. Appl. No. 11/750,600.
Office Action mailed Jun. 24, 2009 in U.S. Appl. No. 12/055,433.
Final Office Action mailed Feb. 23, 2010 in U.S. Appl. No. 12/055,433.
Office Action dated Jun. 1, 2010 in U.S. Appl. No. 12/488,079.
New England Journal of Medicine, vol. 342:505-507, 2001.
Merck Manuals Online Medical Library, www.merck.com, 2007.
Cleeves et al., "Trazodone is ineffective in essential tremor", J. Neurol Nerusurg Psychiatry, 1990, 53:268-269.

Robinson et al. "Pregablin not Effective for Essential Tremor", www.medpagetoday.com, 2009.
Koller et al., "Essential Tremor Variants: Effect of Treatment", abstract, Clinical Pharmacology, 1987.
Aron et al., Neuropharmacology, 10, 459-469, 1971.
Handley and Mithani, Naunyn. Schmied. Arch. Pharmacol., 327, 1-5, 1984.
Meert et al., Pharmacol. Biochem. Behav.; 2005, 80(2), pp. 309-326.
Notice of Allowance mailed Oct. 22, 2010 in U.S. Appl. No. 11/154,386.
Notice of Allowance mailed Nov. 29, 2010 in U.S. Appl. No. 11/406,794.
Notice of Allowance mailed Aug. 12, 2010 in U.S. Appl. No. 11/611,961.
Notice of Allowance mailed Nov. 30, 2010 in U.S. Appl. No. 11/611,961.
Notice of Allowance mailed Nov. 15, 2010 in U.S. Appl. No. 11/612,202.
Notice of Allowance mailed Dec. 15, 2010 in U.S. Appl. No. 11/674,021.
Notice of Allowance mailed Dec. 15, 2010 in U.S. Appl. No. 11/750,600.
Notice of Allowance mailed Dec. 14, 2010 in U.S. Appl. No. 12/488,079.
Pansare et al., Intramolecular imine cross-coupling in dibenzylidine sulphamides: synthesis of unsymmetrical 1,2-diaryl ethanediamines, Tetrahedron Letters, v. 37, N. 16, p. 2859-2862, (2005).
Whitehead et al., Diuretics.II. Alkoxymercuration oby mixed anion salts of mercury, Journal of the American Chemical Society, v. 80, N. 9, p. 2182-2185, (1958).
Kim et al., Tet Lett, 23(14), pp. 1505-1508, (1982).
Johns Hopkins Clinical Trial of Topiramate for Cocaine Addiction (ClinicalTrials.gov), (2009).
Notice of Allowance dated Jan. 11, 2011 in U.S. Appl. No. 11/209,122.
Notice of Allowance dated Mar. 14, 2011 in U.S. Appl. No. 11/406,794.
Notice of Allowance dated Mar. 14, 2011 in U.S. Appl. No. 11/611,961.
Notice of Allowance mailed Mar. 4, 2011 in U.S. Appl. No. 11/612,202.
Office Action mailed Apr. 12, 2011 in U.S. Appl. No. 11/612,222.
Office Action mailed Oct. 15, 2010 in U.S. Appl. No. 11/612,249.
Office Action mailed Apr. 22, 2011 in U.S. Appl. No. 11/612,249.
Office Action mailed Sep. 22, 2010 in U.S. Appl. No. 12/055,433.
Office Action mailed Nov. 15, 2010 in U.S. Appl. No. 12/055,924.
MacDonald et al., CNS Drugs, 2002, 16(8): 549-562.
Walden et al., Neuropsychobiology, 1998,38: 181-84.
Byrn et al., Pharmaceutical Research, Kluwer Academic Publishers, New York, NY, US, vol. 12, No. 7, 1995, pp. 945-954.
Bernando, L., Prevention of epilepsy after head trauma: do we need drugs or a new approach?, 2003, Epilepsia, 44, (Suppl. 10), 27-33.
D'Ambrosio et al., Curr. Opin. Neurol. Dec. 2004; 17(6): 731-735.
Jones et al. "Screening for Major Depression in Epilepsy with Common Self-Report Depression Inventories", Epilepsia, May 2005; 46(5):731-735.
Kane et al., Psychopharmacological Bulletin, vol. 24, pp. 62-67 (1988).
Kaplan & Sadock's Comprehensive Textbook of Psychiatry, Seventh Edition, vol. II, Lippincott Williams & Wilkins: Philadelphia, pp. 2467-2468, 2000.
Kaplan & Sadock's Comprehensive Textbook of Psychiatry, Seventh Edition, vol. II, Lippincott Williams & Wilkins: Philadelphia, pp. 2470-2471, 2000.
Physician's Desk Reference; Kaplan & Sadock's Comprehensive Textbook of Psychiatry, Seventh Edition, vol. II, Lippincott Williams & Wilkins: Philadelphia, pp. 2466-2467, 2000 (olanzapine).
Physician's Desk Reference; Kaplan & Sadock's Comprehensive Textbook of Psychiatry, Seventh Edition, vol. II, Lippincott Williams & Wilkins: Philadelphia, pp. 2456-2463, 2000 (clozapine).
Physician's Desk Reference; Kaplan & Sadock's Comprehensive Textbook of Psychiatry, Seventh Edition, vol. II, Lippincott Williams & Wilkins: Philadelphia, pp. 2463-2466, 2000 (risperidone).
Physician's Desk Reference; Kaplan & Sadock's Comprehensive Textbook of Psychiatry, Seventh Edition, vol. II, Lippincott Williams & Wilkins: Philadelphia, pp. 2469-2470, 2000 (quetiapine).
Notice of Allowance dated Jun. 1, 2011 in U.S. Appl. No. 11/209,122.
Notice of Allowance dated Jun. 30, 2011 in U.S. Appl. No. 11/406,794.
Notice of Allowance dated Jul. 18, 2011 in U.S. Appl. No. 11/611,961.
Office Action mailed Jul. 11, 2011 in U.S. Appl. No. 12/431,141.
Office Action mailed Jun. 8, 2011 in U.S. Appl. No. 12/055,433.
Office Action mailed May 26, 2011 in U.S. Appl. No. 12/055,695.
Notice of Allowance mailed Apr. 12, 2011 in U.S. Appl. No. 12/055,924.
Notice of Allowance mailed Jun. 21, 2011 in U.S. Appl. No. 12/488,079.

SULFAMATE AND SULFAMIDE DERIVATIVES USEFUL FOR THE TREATMENT OF EPILEPSY AND RELATED DISORDERS

CROSS REFERENCE TO RELATED APPLICATIONS

This application claims the benefit of U.S. Provisional Application 60/580,178, filed on Jun. 16, 2004, which is incorporated by reference herein in its entirety.

FIELD OF THE INVENTION

The present invention is directed to novel sulfamate and sulfamide derivatives, pharmaceutical compositions containing them and their use in the treatment of epilepsy and related disorders.

BACKGROUND OF THE INVENTION

Epilepsy describes a condition in which a person has recurrent seizures due to a chronic, underlying process. Epilepsy refers to a clinical phenomenon rather than a single disease entity, since there are many forms and causes of epilepsy. Using a definition of epilepsy as two or more unprovoked seizures, the incidence of epilepsy is estimated at approximately 0.3 to 0.5 percent in different populations throughout the world, with the prevalence of epilepsy estimated at 5 to 10 people per 1000.

An essential step in the evaluation and management of a patient with a seizure is to determine the type of seizure that has occurred. The main characteristic that distinguishes the different categories of seizures is whether the seizure activity is partial (synonymous with focal) or generalized.

Partial seizures are those in which the seizure activity is restricted to discrete areas of the cerebral cortex. If consciousness is fully preserved during the seizure, the clinical manifestations are considered relatively simple and the seizure is termed a simple-partial seizure. If consciousness is impaired, the seizure is termed a complex-partial seizure. An important additional subgroup comprises those seizures that begin as partial seizures and then spread diffusely throughout the cortex, which are known as partial seizures with secondary generalization.

Generalized seizures involve diffuse regions of the brain simultaneously in a bilaterally symmetric fashion. Absence or petit mal seizures are characterized by sudden, brief lapses of consciousness without loss of postural control. Atypical absence seizures typically include a longer duration in the lapse of consciousness, less abrupt onset and cessation, and more obvious motor signs that may include focal or lateralizing features. Generalized Tonic-clonic or grand mal seizures, the main type of generalized seizures, are characterized by abrupt onset, without warning. The initial phase of the seizure is usually tonic contraction of muscles, impaired respiration, a marked enhancement of sympathetic tone leading to increased heart rate, blood pressure, and pupillary size. After 10-20 s, the tonic phase of the seizure typically evolves into the clonic phase, produced by the superimposition of periods of muscle relaxation on the tonic muscle contraction. The periods of relaxation progressively increase until the end of the ictal phase, which usually lasts no more than 1 min. The postictal phase is characterized by unresponsiveness, muscular flaccidity, and excessive salivation that can cause stridorous breathing and partial airway obstruction. Atonic seizures are characterized by sudden loss of postural muscle tone lasting 1-2 s. Consciousness is briefly impaired, but there is usually no postictal confusion. Myoclonic seizures are characterized by a sudden and brief muscle contraction that may involve one part of the body or the entire body. (www.harrisonsonline.com, Mar. 29, 2001)

Carbonic anhydrase inhibitors (CAIs) have been widely used in medicine, mainly as antiglaucoma and antisecretory drugs or diuretic agents, and are valuable compounds. However, systemic antiglaucoma agents (such as acetazolamide) possess potentially unwanted side-effects including paresthesias, nephrolithiasis and weight loss. Topiramate is a well known anticonvulsant drug that possesses single digit micromolar carbonic anhydrase inhibition, which is suspected as the cause of paresthesias noted by some patients taking topiramate.

There remains a need to provide an effective treatment for epilepsy and related disorders, and preferably treatment which does not have the associated side-effects attributable to carbonic anhydrase inhibition.

SUMMARY OF THE INVENTION

The present invention is directed to novel sulfamate and sulfamide derivatives, pharmaceutical compositions containing them and their use in the treatment of epilepsy and related disorders. More particularly, the present invention is direction to compounds of formula (I) and compounds of formula (II) as hereinafter defined.

The present invention is directed to novel sulfamate derivatives, compounds of formula (I)

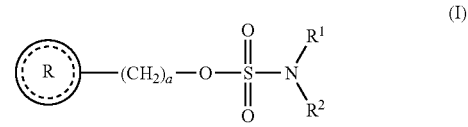

wherein $R^1$ and $R^2$ are each independently selected from the group consisting of hydrogen and lower alkyl;

a is an integer from 1 to 2;

is a ring structure selected from the group consisting of

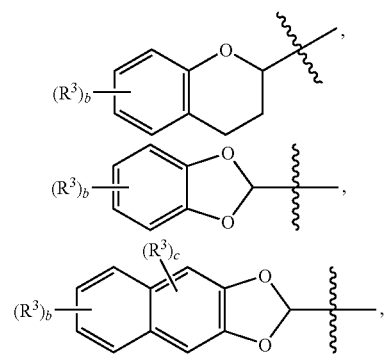

-continued

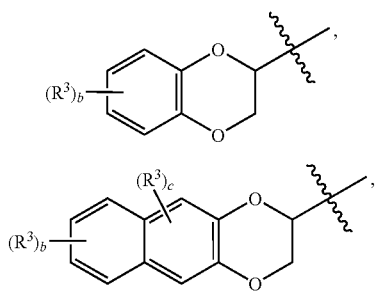

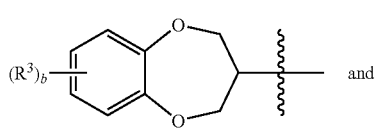

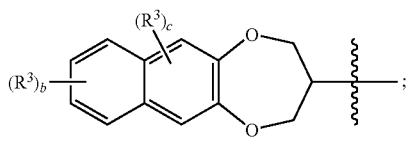 and

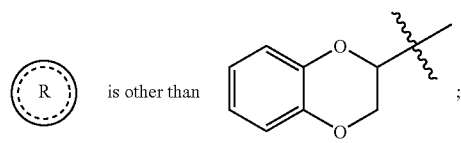;

wherein b is an integer from 0 to 4; and wherein c is an integer from 0 to 2;

each $R^3$ is independently selected form the group consisting of halogen, lower alkyl, hydroxy substituted lower alkyl, —O-(lower alkyl), —S-(lower alkyl), nitro, cyano, amino, lower alkylamino, di(lower alkyl)amino and —C(O)O-(lower alkyl);

provided that when

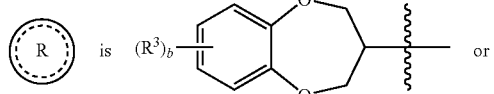 or

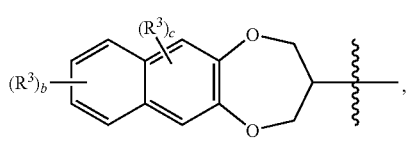, then a is 1;

provided further that when $R^1$ is hydrogen, $R^2$ is hydrogen and a is 1, then

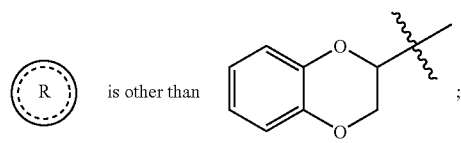;

or a pharmaceutically acceptable salt thereof.

The present invention is further directed to novel sulfamide derivatives, compounds of formula (II)

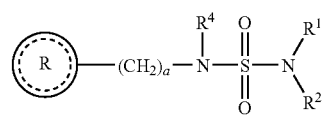

wherein $R^1$ and $R^2$ are each independently selected from the group consisting of hydrogen and lower alkyl;

$R^4$ is selected from the group consisting of hydrogen and lower alkyl;

a is an integer from 1 to 2;

is selected from the group consisting of

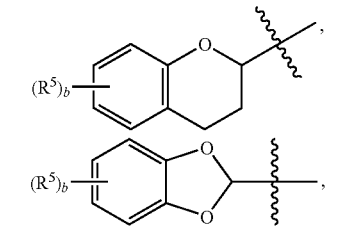

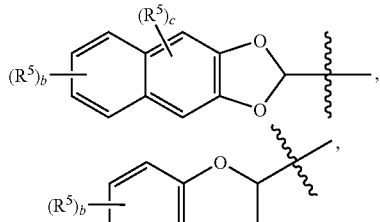

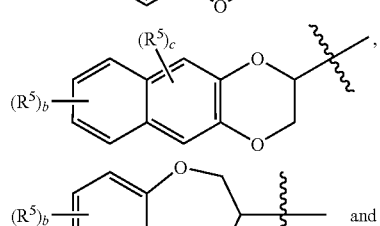 and

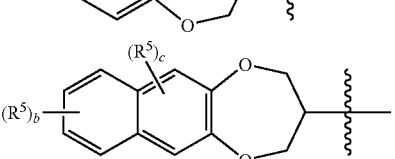;

wherein b is an integer from 0 to 4; and wherein c is an integer from 0 to 2;

each $R^5$ is independently selected from the group consisting of halogen, lower alkyl and nitro;

provided that when

is

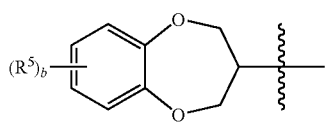

or

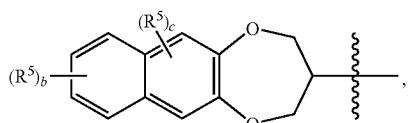

then a is 1;

or a pharmaceutically acceptable salt thereof.

The present invention is further directed to a compound of formula (III)

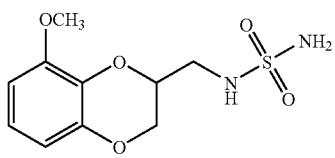

or a pharmaceutically acceptable salt thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention is a method of treating epilepsy and related disorders in a subject in need thereof comprising administering to the subject a therapeutically effective amount of any of the compounds or pharmaceutical compositions described above.

Another example of the invention is the use of any of the compounds described herein in the preparation of a medicament for treating epilepsy or a related disorder, in a subject in need thereof.

DETAILED DESCRIPTION OF THE INVENTION

The present invention is directed to compounds of formula (I) and compounds of formula (II)

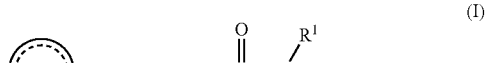

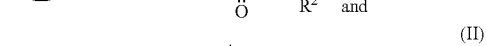

wherein

a, $R^1$, $R^2$ and $R^4$ are as herein defined. The present invention is further directed to a compound of formula (III). The compounds of formula (I), formula (II) and formula (III) are useful for treating epilepsy and related disorders.

As used herein, unless otherwise noted, "halogen" shall mean chlorine, bromine, fluorine and iodine.

As used herein, unless otherwise noted, the term "alkyl" whether used alone or as part of a substituent group, includes straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, the notation "*" shall denote the presence of a stereogenic center.

When a particular group is "substituted" (e.g., alkyl, aryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenyl-alkyl-amino-carbonyl-alkyl" substituent refers to a group of the formula

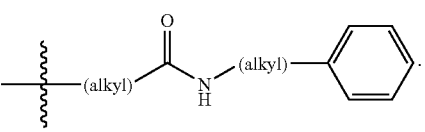

Abbreviations used in the specification, particularly the Schemes and Examples, are as follows:
DCC=Dicyclohexyl Carbodiimide
DCE =Dichloroethane
DCM=Dichloromethane
DIPEA or DIEA=Diisopropylethylamine
DMF=N,N-Dimethylformamide
DMSO=Dimethylsulfoxide
EDC=Ethylcarbodiimide
$Et_3N$ or TEA=Triethylamine
$Et_2O$=Diethyl ether
EA or EtOAc=Ethyl acetate
EtOH=Ethanol
IPA=2-propanol
Hept=Heptane
HOBT=1-Hydroxybenzotriazole
HPLC=High Pressure Liquid Chromatography
LAH=Lithium Aluminum Hydride
M or MeOH=Methanol
NMR=Nuclear Magnetic Resonance
Pd—C=Palladium on Carbon Catalyst
RP HPLC=Reverse Phase High Pressure Liquid Chromatography
RT or rt=Room temperature
TEA=Triethylamine
TFA=Trifluoroacetic Acid
THF=Tetrahydrofuran
TLC=Thin Layer Chromatography As used herein, unless otherwise noted, the terms "epilepsy and related disorders" or "epilepsy or related disorder" shall mean any disorder in which a subject (preferably a human adult, child or infant) experiences one or more seizures and/or tremors. Suitable examples include, but are not limited to, epilepsy (including, but not limited to, localization-related epilepsies, generalized epilepsies, epilepsies with both generalized and local seizures, and the like), seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, and the like), essential tremor, restless limb syndrome, and the like. Preferably, the disorder is selected from epilepsy (regardless of type, underlying cause or origin), essential tremor or restless limb syndrome, more preferably, the disorder is epilepsy (regardless of type, underlying cause or origin) or essential tremor.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in *Design of Prodrugs*, ed. H. Bundgaard, Elsevier, 1985.

The present invention provides pharmaceutical compositions comprising a compound of formula (I), a compound of formula (II) and/or a compound of formula (III) in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of the principle ingredient. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 1 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

To prepare the pharmaceutical compositions of this invention, a compound of formula (I), a compound of formula (II) and/or a compound of formula (III) is intimately admixed with a pharmaceutical carrier according to conventional pharmaceutical compounding techniques, which carrier may take a wide variety of forms depending on the form of preparation desired for administration, e.g., i.v. sterile injectable formulations will be prepared using appropriate solubilizing agents. A unit dose would contain about 10 to about 300 mg of the active ingredient. The tablets contain some or all of the following inactive ingredients: lactose hydrous, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide, and polysorbate 80. One skilled in the art will recognize that oral tablets containing a compound of formula (I), a compound of formula (II) and/or a compound of formula (III) may be similarly prepared and may contain similar inactive ingredients.

One skilled in the art will recognize that pharmaceutical compositions comprising more than one active ingredient may be similarly prepared according to known methods.

In an embodiment of the present invention $R^1$ is selected from the group consisting of hydrogen and methyl. In another embodiment of the present invention $R^2$ is selected from the group consisting of hydrogen and methyl. In yet another embodiment of the present invention $R^1$ and $R^2$ are each hydrogen or $R^1$ and $R^2$ are each methyl.

In an embodiment of the present invention —$(CH_2)_a$— is selected from the group consisting of —$CH_2$— and —$CH_2$—$CH_2$—. In another embodiment of the present invention —$(CH_2)_a$— is —$CH_2$—.

In an embodiment of the present $R^4$ is selected from the group consisting of hydrogen and methyl, preferably, $R^4$ is hydrogen.

In an embodiment of the present invention a is 1.

In an embodiment of the present invention b is an integer from 0 to 2. In another embodiment of the present invention c is an integer from 0 to 2. In another embodiment of the present invention b is an integer from 0 to 1. In another embodiment of the present invention c is an integer from 0 to 1. In yet another embodiment of the present invention the sum of b and c is an integer form 0 to 2, preferably an integer form 0 to 1. In yet another embodiment of the present invention b is an integer from 0 to 2 and c is 0.

In an embodiment of the present invention,

is a ring structure selected from the group consisting of

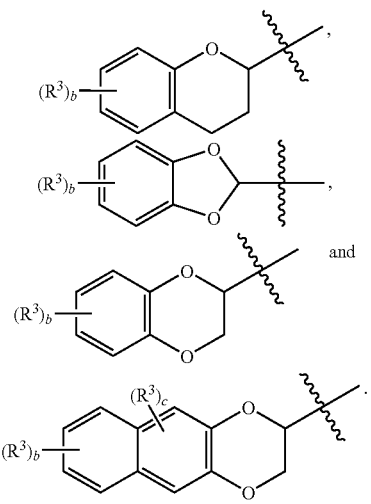

In another embodiment of the present invention,

is a ring structure selected from the group consisting of

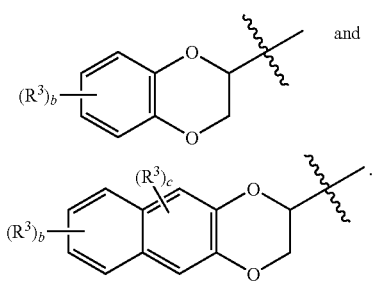

In an embodiment of the present invention,

is a ring structure selected from the group consisting of 2-(chromanyl), 2-(6-chloro-2,3-dihydro-benzo[1,4]dioxinyl), 2-(benzo[1,3]dioxolyl), 2-(5-chloro-2,3-dihydro-benzo[1,4]dioxinyl), 2-(7-nitro-2,3-dihydro-benzo[1,4]dioxinyl), 2-(6,7-dichloro-2,3-dihydro-benzo[1,4]dioxinyl), 2-(2,3-dihydro-naphtho[2,3-b][1,4]dioxinyl) and 2-(7-chloro-benzo[1,3]dioxolyl). In another embodiment of the present invention,

is a ring structure selected from the group consisting of 2-(5-chloro-2,3-dihydro-benzo[1,4]dioxinyl), 2-(7-nitro-2,3-dihydro-benzo[1,4]dioxinyl), 2-(6,7-dichloro-2,3-dihydro-benzo[1,4]dioxinyl) and 2-(2,3-dihydro-naphtho[2,3-b][1,4]dioxinyl).

In an embodiment of the present invention,

is selected from the group consisting of

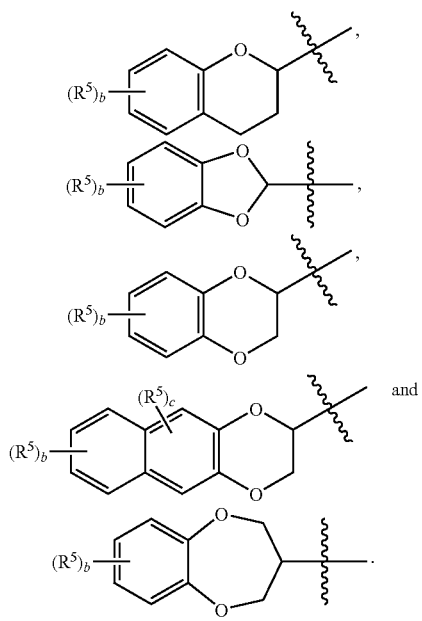

In another embodiment of the present invention,

is selected from the group consisting of

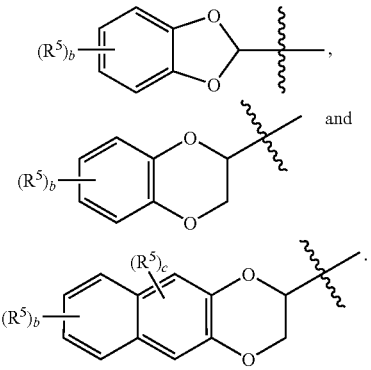

In an embodiment of the present invention,

is selected from the group consisting of 2-(2,3-dihydro-benzo[1,4]dioxinyl), 2-(benzo[1,3]dioxolyl), 3-(3,4-dihydro-benzo[1,4]dioxepinyl), 2-(6-chloro-2,3-dihydro-benzo[1,4]dioxinyl), 2-(6-fluoro-2,3-dihydro-benzo[1,4]dioxinyl), 2-(chromanyl), 2-(5-fluoro-2,3-dihydro-benzo[1,4]dioxinyl), 2-(7-chloro-2,3-dihydro-benzo[1,4]dioxinyl), 2-(6-chloro-benzo[1,3]dioxolyl), 2-(7-nitro-2,3-dihydro-benzo[1,4]dioxinyl), 2-(7-methyl-2,3-dihydro-benzo[1,4]dioxinyl), 2-(5-chloro-2,3-dihydro-benzo[1,4]dioxinyl), 2-(6-bromo-2,3-dihydro-benzo[1,4]dioxinyl), 2-(6,7-dichloro-2,3-dihydro-benzo[1,4]dioxinyl), 2-(8-chloro-2,3-dihydro-benzo[1,4]dioxinyl), 2-(2,3-dihydro-naphtho[2,3-b][1,4]dioxinyl) and 2-(4-methyl-benzo[1,3]dioxolyl).

In another embodiment of the present invention,

is selected from the group consisting 2-(benzo[1,3]dioxolyl), 2-(2,3-dihydro-benzo[1,4]dioxinyl), 2-(6-chloro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(6-bromo-2,3-dihydro-benzo[1,4]dioxinyl) and 2-(6,7-dichloro-2,3-dihydro-benzo[1,4]dioxinyl). In another embodiment of the present invention,

is selected from the group consisting of 2-(2,3-dihydro-benzo[1,4]dioxinyl), 2-(7-methyl-2,3-dihydro-benzo[1,4]dioxinyl) and 2-(6-bromo-2,3-dihydro-benzo[1,4]dioxinyl).

In an embodiment of the present invention $R^3$ is selected from the group consisting of halogen, lower alkyl, hydroxy substituted lower alkyl, —O-(lower alkyl), nitro, cyano, amino, lower alkylamino and di(lower alkyl)amino. In another embodiment of the present invention $R^3$ is selected from the group consisting of halogen and nitro. In another embodiment of the present invention $R^3$ is selected from the group consisting of chloro and nitro.

In an embodiment of the present invention R$^5$ is selected from the group consisting of (II) halogen and lower alkyl. In another embodiment of the present invention R$^5$ is selected from chloro, fluoro, bromo and methyl.

In an embodiment of the present invention, in the compound of formula (I),

is other than

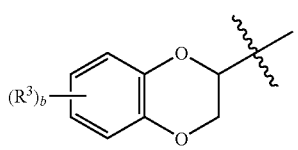

wherein b is 1 and R$^3$ is selected from the group consisting of halogen, nitro, cyano, amino, lower alkyl, lower alkoxy and —C(O)O-(lower alkyl). In another embodiment of the present invention, in the compound of formula (I),

is other than

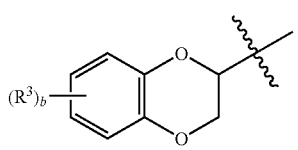

wherein b is 1.

In an embodiment of the present invention, the stereo-center on the compound of formula (I) is in the S-configuration. In another embodiment of the present invention, the stereo-center on the compound of formula (I) is in the R-configuration.

In an embodiment of the present invention, the stereo-center on the compound of formula (II) is in the S-configuration. In another embodiment of the present invention, the stereo-center on the compound of formula (II) is in the R-configuration.

In an embodiment of the present invention the compound of formula (I) is present as an enantiomerically enriched mixture, wherein the % enantiomeric enrichment (% ee) is greater than about 75%, preferably greater than about 90%, more preferably greater than about 95%, most preferably greater than about 98%.

In an embodiment of the present invention the compound of formula (II) is present as an enantiomerically enriched mixture, wherein the % enantiomeric enrichment (% ee) is greater than about 75%, preferably greater than about 90%, more preferably greater than about 95%, most preferably greater than about 98%.

In an embodiment of the present invention are compounds of formula (I) wherein the MES activity at 100 mg/kg is greater than or equal to 3/5 mice. In another embodiment of the present invention are compounds of formula (II) wherein the MES activity at 100 mg/kg is greater than or equal to 3/5 mice.

Representative compounds of the present invention, are as listed in Tables 1 and 2 below. Additional compounds of the present invention are as listed in Table 3. In Tables 1, 2 and 3 below, the column headed "stereo" defines the stereo-configuration at the carbon atom of the heterocycle attached at the starred bond. Where no designation is listed, the compound was prepared as a mixture of stereo-configurations. Where an "R" or "S" designation is listed, the stereo-configuration was based on the enantiomerically enriched starting material.

TABLE 1

Representative Compounds of Formula (I)

| ID No. | R | Stereo | (CH$_2$)$_a$ | R$^1$ | R$^2$ |
|---|---|---|---|---|---|
| 11 | 2-(chromanyl) | | CH$_2$ | H | H |
| 12 | 2-(6-chloro-2,3-dihydro-benzo[1,4]dioxinyl) | R | CH$_2$ | H | H |
| 17 | 2-(benzo[1,3]dioxolyl) | | CH$_2$ | H | H |
| 21 | 2-(5-chloro-2,3-dihydro-benzo[1,4]dioxinyl) | R | CH$_2$ | H | H |
| 25 | 2-(7-nitro-2,3-dihydro-benzo[1,4]dioxinyl) | R | CH$_2$ | H | H |
| 27 | 2-(6,7-dichloro-2,3-dihydro-benzo[1,4]dioxinyl) | R | CH$_2$ | H | H |
| 28 | 2-(2,3-dihydro-naphtho[2,3-b][1,4]dioxinyl) | R | CH$_2$ | H | H |
| 31 | 2-(7-chloro-benzo[1,3]dioxolyl) | | CH$_2$ | H | H |

TABLE 2

Representative Compounds of Formula (II)

| ID No. | R | Stereo | (CH$_2$)$_a$ | NR$^4$ | R$^1$ | R$^2$ |
|---|---|---|---|---|---|---|
| 1 | 2-(2,3-dihydro-benzo[1,4]dioxinyl) | | CH$_2$ | NH | H | H |
| 2 | 2-(benzo[1,3]dioxolyl) | | CH$_2$ | NH | H | H |

TABLE 2-continued

Representative Compounds of Formula (II)

| ID No. | R | Stereo | (CH$_2$)$_a$ | NR$^4$ | R$^1$ | R$^2$ |
|---|---|---|---|---|---|---|
| 3 | 3-(3,4-dihydro-2H-benzo[1,4]dioxepinyl) | | CH$_2$ | NH | H | H |
| 4 | 2-(2,3-dihydro-benzo[1,4]dioxinyl) | S | CH$_2$ | NH | H | H |
| 5 | 2-(2,3-dihydro-benzo[1,4]dioxinyl) | R | CH$_2$ | NH | H | H |
| 6 | 2-(2,3-dihydro-benzo[1,4]dioxinyl) | | CH$_2$ | NH | methyl | methyl |
| 7 | 2-(2,3-dihydro-benzo[1,4]dioxinyl) | | CH$_2$ | N(CH$_3$) | H | H |
| 8 | 2-(6-chloro-2,3-dihydro-benzo[1,4]dioxinyl) | S | CH$_2$ | NH | H | H |
| 9 | 2-(6-fluoro-2,3-dihydro-benzo[1,4]dioxinyl) | S | CH$_2$ | NH | H | H |
| 10 | 2-(chromanyl) | | CH$_2$ | NH | H | H |
| 13 | 2-(5-fluoro-2,3-dihydro-benzo[1,4]dioxinyl) | S | CH$_2$ | NH | H | H |
| 14 | 2-(7-chloro-2,3-dihydro-benzo[1,4]dioxinyl) | S | CH$_2$ | NH | H | H |
| 15 | 2-(6-chloro-benzo[1,3]dioxolyl) | | CH$_2$ | NH | H | H |
| 16 | 2-(2,3-dihydro-benzo[1,4]dioxinyl) | | CH$_2$CH$_2$ | NH | H | H |
| 18 | 2-(7-nitro-2,3-dihydro-benzo[1,4]dioxinyl) | S | CH$_2$ | NH | H | H |
| 19 | 2-(7-methyl-2,3-dihydro-benzo[1,4]dioxinyl) | S | CH$_2$ | NH | H | H |
| 20 | 2-(5-chloro-2,3-dihydro-benzo[1,4]dioxinyl) | S | CH$_2$ | NH | H | H |
| 22 | 2-(8-methoxy-2,3-dihydro-benzo[1,4]dioxinyl) | S | CH$_2$ | NH | H | H |
| 24 | 2-(6-bromo-2,3-dihydro-benzo[1,4]dioxinyl) | S | CH$_2$ | NH | H | H |
| 29 | 2-(6,7-dichloro-2,3-dihydro-benzo[1,4]dioxinyl) | S | CH$_2$ | NH | H | H |
| 30 | 2-(8-chloro-2,3-dihydro-benzo[1,4]dioxinyl) | S | CH$_2$ | NH | H | H |
| 33 | 2-(2,3-dihydro-naphtho[2,3-b][1,4]dioxinyl) | S | CH$_2$ | NH | H | H |
| 35 | 2-(4-methyl-benzo[1,3]dioxolyl) | | CH$_2$ | NH | H | H |

TABLE 3

Additional Compounds of the Present Invention

| ID No. | Y | Stereo | X | NR$^{14}$ | R$^{11}$ | R$^{12}$ |
|---|---|---|---|---|---|---|
| 23 | 2-(5-methoxy-2,3-dihydro-benzo[1,4]dioxinyl) | S | CH$_2$ | NH | H | H |
| 26 | 2-(6-methylcarbonyl-2,3-dihydro-benzo[1,4]dioxinyl) | S | CH$_2$ | NH | H | H |
| 32 | 2-(6-methoxycarbonyl-2,3-dihydro-benzo[1,4]dioxinyl) | S | CH$_2$ | NH | H | H |
| 34 | 2-(6-hydroxymethyl-2,3-dihydro-benzo[1,4]dioxinyl) | S | CH$_2$ | NH | H | H |

TABLE 3-continued

Additional Compounds of the Present Invention

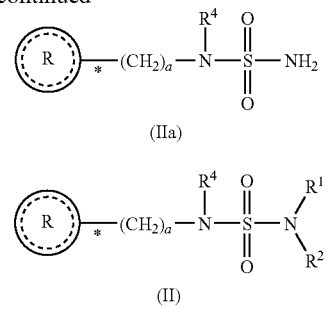

| ID No. | Y | Stereo | X | NR$^{14}$ | R$^{11}$ | R$^{12}$ |
|---|---|---|---|---|---|---|
| 36 | 2-(7-amino-2,3-dihydro-benzo[1,4]dioxinyl) | S | CH$_2$ | NH | H | H |

Compounds of formula (I) may be prepared according to the process outlined in Scheme 1.

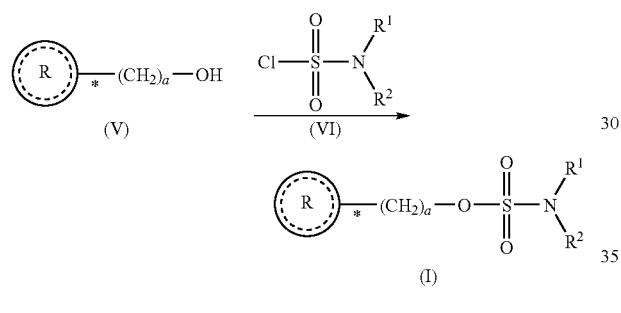

Accordingly, a suitably substituted compound of formula (V), a known compound or compound prepared by known methods, is reacted with a suitably substituted compound of formula (VI), a known compound or compound prepared by known methods, in the presence of a base such as NaH, TEA, DIPEA, pyridine, and the like, in an organic solvent such as DMF, DMSO, and the like, to yield the corresponding compound of formula (I).

Compounds of formula (II) may be prepared according to the process outlined in Scheme 2.

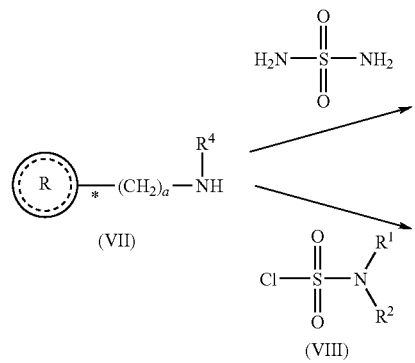

Accordingly, a suitably substituted compound of formula (VII), a known compound or compound prepared by known methods, is reacted with sulfamide, a known compound, preferably wherein the sulfamide is present in an amount in the range of about 2 to about 5 equivalents, in an organic solvent such as THF, dioxane, and the like, preferably at an elevated temperature in the range of about 50° C. to about 100° C., more preferably at about reflux temperature, to yield the corresponding compound of formula (IIa).

Alternatively, a suitably substituted compound of formula (VII), a known compound or compound prepared by known methods, is reacted with a suitably substituted compound of formula (VIII), a known compound or compound prepared by known methods, in the presence of a base such as TEA, DIPEA, pyridine, and the like, in an organic solvent such as DMF, DMSO, and the like, to yield the corresponding compound of formula (II).

Compounds of formula (V) wherein

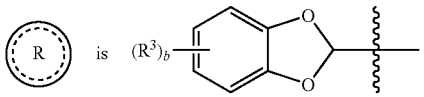

may be prepared according to the process outlined in Scheme 3.

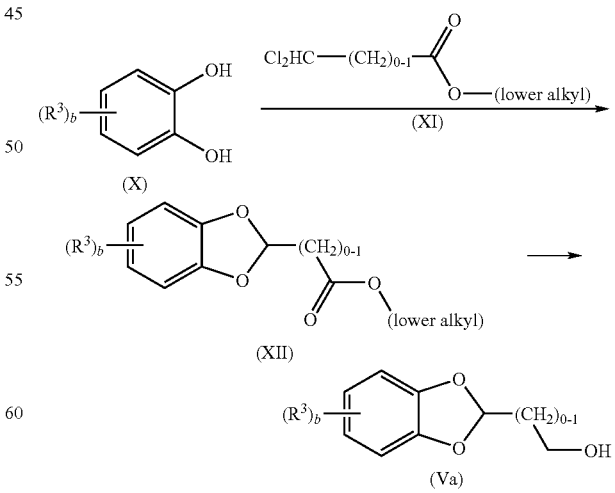

Accordingly, a suitably substituted compound of formula (X), a known compound or compound prepared by known methods, is reacted with a suitably substituted compound of formula (XI), a known compound or compound prepared by known methods, in the presence of a base such as sodium methoxide, sodium ethoxide, sodium t-butoxide, potassium methoxide, potassium t-butoxide, and the like, in an organic solvent such as methanol, ethanol, IPA, and the like, preferably at an elevated temperature in the range of about 50° C. to about 100° C., more preferably at about reflux temperature, to yield the corresponding compound of formula (XII).

The compound of formula (XII) is reacted with a suitably selected reducing agent, such as LAH, and the like, in an organic solvent such as THF, diethyl ether, and the like, to yield the corresponding compound of formula (Va).

Compounds of formula (VII) wherein

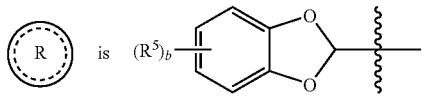

may be prepared according to the process outlined in Scheme 4.

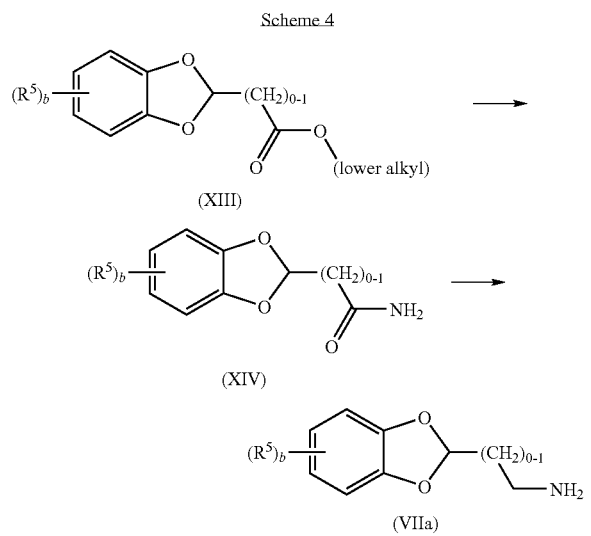

Accordingly, a suitably substituted compound of formula (XIII), a known compound or compound prepared by known method (for example as described in Scheme 3 above) is reacted with $NH_4OH$, a known compound, optionally in an organic solvent such as acetonitrile, and the like, to yield the corresponding compound of formula (XIV).

The compound of formula (XIV) is reacted with a suitably selected reducing agent, such as LAH, and the like, and the like, in an organic solvent such as THF, diethyl ether, and the like, to yield the corresponding compound of formula (VIIa).

Compounds of formula (VII) wherein

is selected from

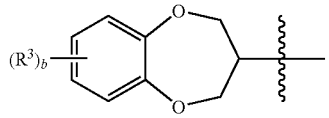

may be prepared according to the process outlined in Scheme 5.

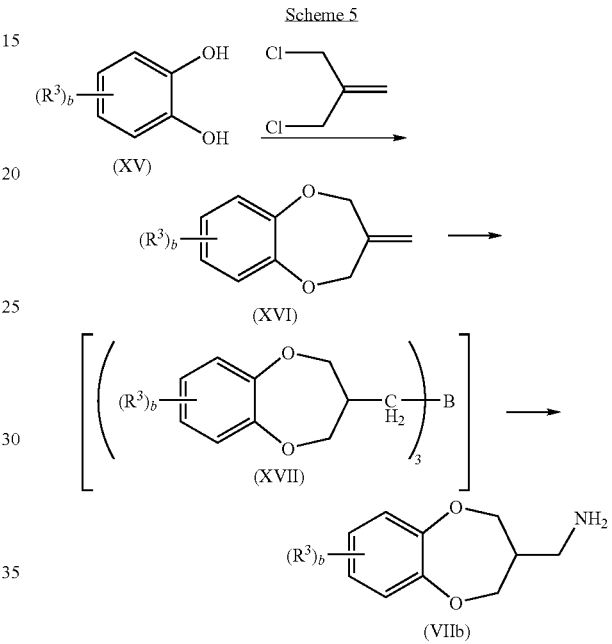

Accordingly, a suitably substituted compound of formula (XV), a known compound or compound prepared by known methods is reacted with 3-chloro-2-chloromethyl-propene, a known compound, in the presence of a base such as potassium carbonate, sodium carbonate, sodium bicarbonate, TEA, DIPEA, and the like, in an organic solvent such as acetonitrile, THF, dioxane, and the like, preferably at an elevated temperature in the range of about 50° C. to about 100° C., more preferably, at about reflux temperature, to yield the corresponding compound of formula (XVI).

The compound of formula (XVI) is reacted with borane, in an organic solvent such as THF, dioxane, and the like, to yield the corresponding compound of formula (XVII), which is preferably not isolated.

The compound of formula (XVII) is reacted with aminosulfonic acid, preferably at an elevated temperature in the range of from about 50° C. to about 100°, more preferably, at about reflux temperature, to yield the corresponding compound of formula (VIIb).

Compounds of formula (V) wherein

is selected from

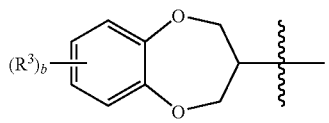

may be prepared according to the process outlined in Scheme 6.

Scheme 6

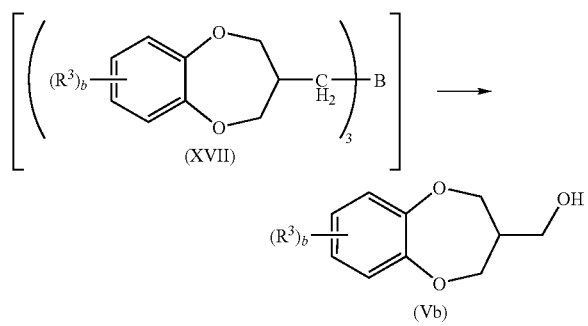

Accordingly, a suitably substituted compound of formula (XVIII), a compound prepared as in Scheme 5 above, is reacted with a peroxide, such as hydrogen peroxide, and the like, in the presence of a base such as NaOH, KOH, and the like, in an organic solvent such as chloroform, DCE, DCM, and the like, to yield the corresponding compound of formula (Vb).

Compounds of formula (V) wherein

is selected from

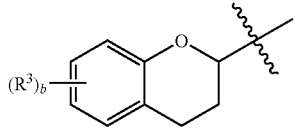

may be prepared according to the process outlined in Scheme 7.

Scheme 7

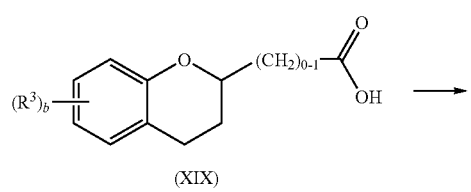

-continued

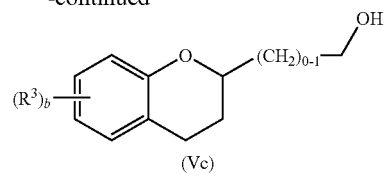

Accordingly, a suitably substituted compound of formula (XIX), a known compound or compound prepared by known methods, is reacted with a suitably selected reducing agent, such as LAH, and the like, in an organic solvent such as THF, diethyl ether, and the like to yield the corresponding compound of formula (Vc).

Compounds of formula (VII) wherein

is selected from

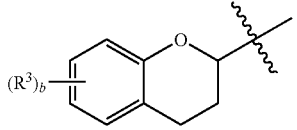

may be prepared according to the process outlined in Scheme 8.

Scheme 8

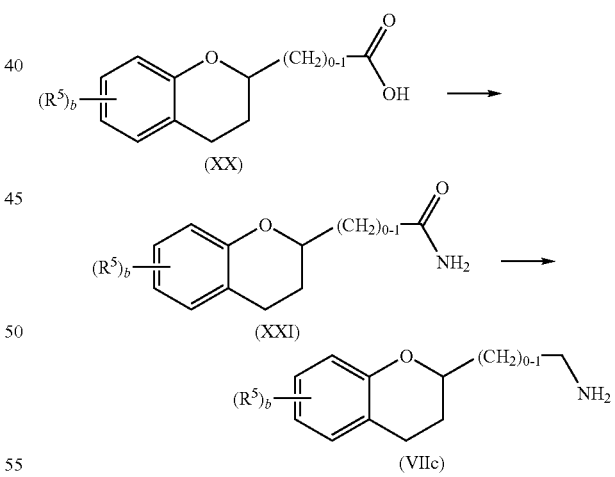

Accordingly, a suitably substituted compound of formula (XX), a known compound or compound prepared by known methods, is reacted with $NH_4OH$, in the presence of a coupling agent such as DCC, and the like, optionally in an organic solvent such as acetonitrile, and the like, to yield the corresponding compound of formula (XXI).

The compound of formula (XXI) is reacted with a suitably selected reducing agent, such as LAH, and the like, in an organic solvent such as THF, diethyl ether, and the like, to yield the corresponding compound of formula (VIIc).

Compounds of formula (V) wherein

is selected from

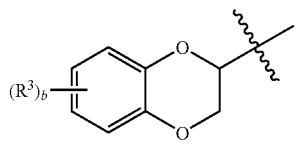

and wherein a is 1, may be prepared according to the process outlined in Scheme 9.

Scheme 9

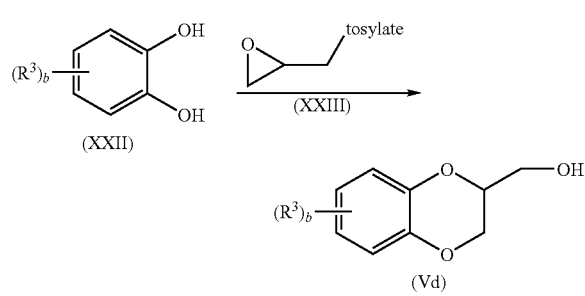

Accordingly, a suitably substituted compound of formula (XXII), a known compound or compound prepared by known methods, is reacted with a suitably substituted compound of formula (XXIII), a known compound or compound prepared by known methods, in the presence of a base such as $K_2CO_3$, $Na_2CO_3$, $NaHCO_3$, and the like, in an organic solvent such as DMF, DMSO, acetonitrile, and the like, preferably, at an elevated temperature in the range of form about 50° C. to about 100° C., more preferably, at an elevated temperature in the range of from about 50° C. to about 75° C., to yield the corresponding compound of formula (Vd).

Compounds of formula (VII) wherein

is selected from

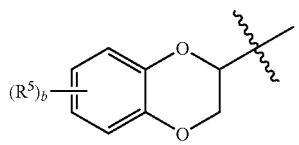

and wherein a is 2, may be prepared according to the process outlined in Scheme 10.

Scheme 10

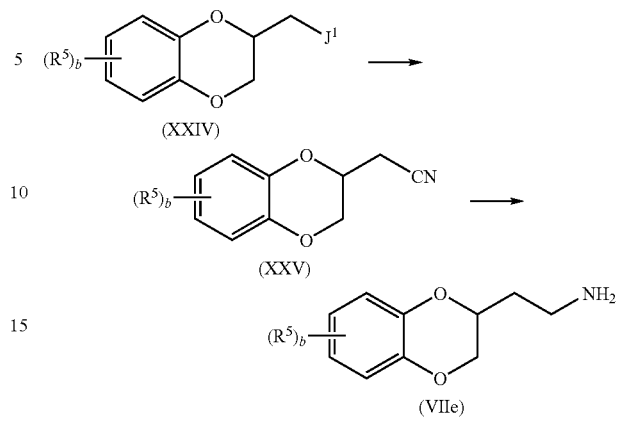

Accordingly, a suitably substituted compound of formula (XXIV) wherein $J^1$ is a suitable leaving group such as Br, Cl, I, tosyl, mesyl, triflyl, and the like, a known compound or compound prepared by known methods (for example, by activating the corresponding compound wherein $J^1$ is OH), is reacted with a cyanide such as potassium cyanide, sodium cyanide, and the like, in an organic solvent such as DMSO, DMF, THF, and the like, to yield the corresponding compound of formula (XXV).

The compound of formula (XXV) is reduced according to known methods, for example by reacting with a suitable reducing agent such as LAH, borane, and the like, to yield the corresponding compound of formula (VIIe).

Compounds of formula (VII) wherein

is selected from

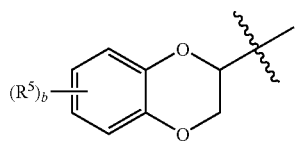

and wherein a is 1, may be prepared according to the process outlined in Scheme 11.

Scheme 11

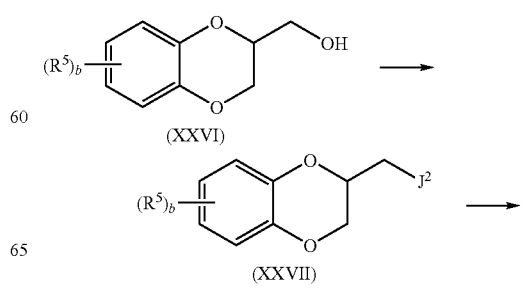

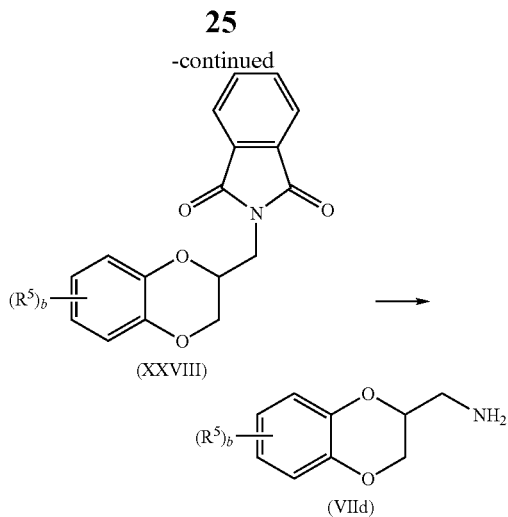

Accordingly, a suitably substituted compound of formula (XXVI), a known compound or compound prepared by known methods (for example according to the process outlined in Scheme 9 above) is activated, according to known method, to yield the corresponding compound of formula (XXVII), wherein $J^2$ is a suitable leaving group, such tosylate, Cl, Br, I, mesylate, triflate, and the like.

The compound of formula (XXVII) is reacted with a phthalimide salt such as potassium phthlimide, sodium phthalimide, and the like, in an organic solvent such as DMF, DMSO, acetonitrile, and the like, preferably, at an elevated temperature in the range of from 50° C. to about 200° C., more preferably, at about reflux temperature, to yield the corresponding compound of formula (XXVIII).

The compound of formula (XXVI) is reacted with $N_2H_4$, a known compound, in an organic solvent such as ethanol, methanol, and the like, preferably, at an elevated temperature in the range of from about 50° C. to about 100° C., more preferably, at about reflux temperature, and the like, to yield the corresponding compound of formula (VIId).

Compounds of formula (V) wherein

is selected from

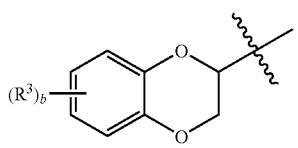

and wherein a is 2, may be similarly prepared according to the process outlined in Scheme 12.

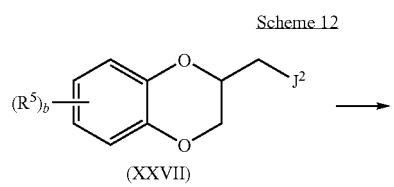

Accordingly, a suitably substituted compound of formula (XXVII) wherein $J^2$ is CN, a known compound or compound prepared by known methods, is hydrolyzed according to known methods, for example by reacting with a suitable acid or base, to yield the corresponding compound of formula (XXIX).

The compound of formula (XXIX) is reduced according to known methods, for example by reacting with a suitable reducing agent such as LAH, and the like, to yield the corresponding compound of formula (Ve).

One skilled in the art will recognize that compounds of formula (V) and (VII) wherein

is selected from

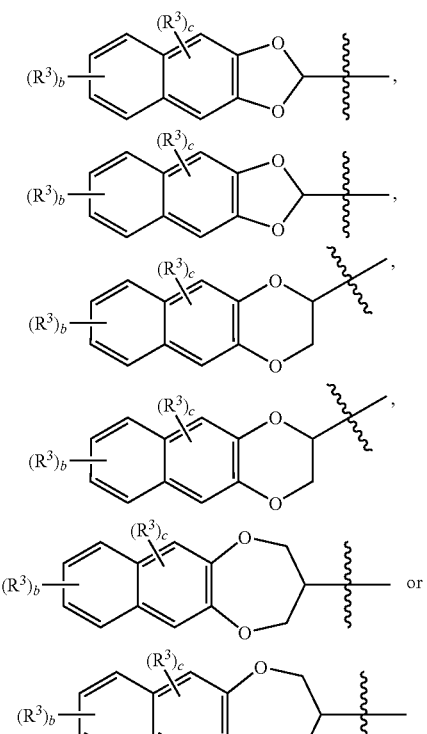

may be similarly prepared according to the processes outlined in Schemes 3 through 12 above, by selecting and substituting the corresponding naphthyl-fused compounds for the benzo-fused starting materials (e.g. the compounds of formula (X), (XIII), (XV), (XVIII), (XIX), (XX), (XXII), (XXIV), etc.).

One skilled in the art will further recognize that wherein a single enantiomer (or a mixture of enantiomers wherein one enantiomer is enriched) of a compound of formula (V) or a compound of formula (VII) is desired, the above processes as described in Schemes 1 through 12 may be applied by substituting the corresponding single enantiomer (or mixture of enantiomers wherein one enantiomer is enriched) for the appropriate starting material.

The following Examples are set forth to aid in the understanding of the invention, and are not intended and should not be construed to limit in any way the invention set forth in the claims which follow thereafter.

EXAMPLE 1

((3,4-Dihydro-2H-benzo[b][1,4]dioxepin-3-yl)methyl)sulfamide (Compound #3)

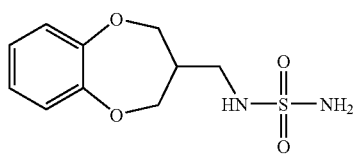

Catechol (5.09 g, 46.2 mmol) and potassium carbonate were combined in acetonitrile and heated to reflux for one hour. 2-Chloromethyl-3-chloro-1-propene (5.78 g, 46.2 mmol) was added and the reaction was continued at reflux for 24 hours. The solution was cooled to room temperature and filtered. The filtrate was evaporated and the residue was diluted with water and extracted with diethyl ether (3×). The combined organic solution was dried over MgSO$_4$ and concentrated. Chromatography (2% ethyl ether in hexane) yielded 3-methylene-3,4-dihydro-2H-benzo[b][1,4]dioxepine as a colorless oil.

MS (ESI): 163.2 (M+H$^+$)

$^1$H NMR (300 MHz, CDCl$_3$), δ: 6.94 (m, 4H), 5.07 (s, 2H), 4.76 (s, 4H).

3-Methylene-3,4-dihydro-2H-benzo[b][1,4]dioxepine (5.00 g, 30.8 mmol) was dissolved in dry THF (100 mL). Borane-THF (1.0 M in THF, 10.3 mL) was added at 0° C. The reaction was stirred at RT for 5 hours. Aminosulfonic acid (6.97 g, 61.6 mmol) was added. The reaction was heated to reflux overnight. The reaction was cooled to room temperature and aqueous sodium hydroxide (3.0 M, 100 mL) was added. The solution was extracted with ethyl acetate (3×100 mL). The combined organic solution was dried over MgSO$_4$. The solution was concentrated under vacuum and purified by chromatography (2% to 8% methanol in dichloromethane) to yield ((3,4-dihydro-2H-benzo[b][1,4]dioxepin-3-yl)methyl) amine as a colorless oil.

MS (ESI): 180.1 (M+H$^+$)

$^1$H NMR (300 MHz, DMSO), δ: 6.92 (m, 4H), 4.21 (m, 2H), 4.07 (m, 2H), 3.33 (broad, 2H), 3.16 (d, J=4Hz, 1H), 2.72 (d, J=4Hz, 1H), 2.30 (m, 1H).

((3,4-Dihydro-2H-benzo[b][1,4]dioxepin-3-yl)methyl) amine (2.90 g, 16.2 mmol) and sulfamide (3.11 g, 32.4 mmol) were combined in dry dioxane (60 ml) and heated to reflux overnight. Chloroform was added and the precipitate was removed by filtration. The filtrate was concentrated under vacuum and purified by chromatography (2% to 8% acetone in dichloromethane) to yield the title compound as an off-white solid.

258.8 (M+H$^+$)

$^1$H NMR (300 MHz, DMSO), δ: 6.92 (m, 4H), 6.71 (broad, 1H), 6.59 (broad, 2H), 4.19 (m, 2H), 4.04 (m, 2H), 3.00 (m, 2H), 2.39 (m, 1H).

EXAMPLE 2

N-(2,3-Dihydro-benzo[1,4]dioxin-2-ylmethyl)-sulfamide (Compound #1)

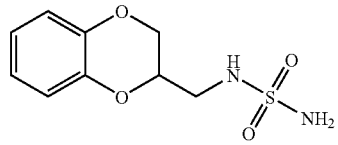

Racemic 2,3-dihydro-1,4-benzdioxin-2-ylmethylamine (4.4 g, 26 mmol) and sulfamide (5.1 g, 53 mmol) were combined in 1,4 dioxane (100 mL) and refluxed for 2 h. The reaction was cooled to room temperature and a small amount of solid was filtered and discarded. The filtrate was evaporated in vacuo and the residue was purified using flash column chromatography (DCM:Methanol—10:1) to yield a white solid. The solid was recrystallized from DCM to yield the title compound as a white solid.

mp: 97.5-98.5° C.

Anal Calc: C, 44.25; H, 4.95; N, 11.47; S, 13.13

Anal Found: C, 44.28; H, 4.66; N, 11.21; S,13.15

H$^1$ NMR (DMSO d6) δ 6.85 (m, 4H), 6.68 (bd s, 3H, NH), 4.28 (m, 2H), 3.97 (dd, J=6.9, 11.4 Hz, 1H), 3.20 (m, 1H), 3.10 (m, 1H).

EXAMPLE 3

(Benzo[1,3]dioxol-2-ylmethyl)sulfamide (Compound #2)

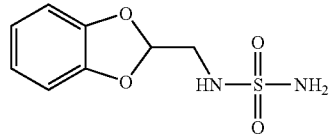

Catechol (10.26 g, 93.2 mmol), sodium methoxide (25% by weight in methanol, 40.3 g, 186 mmol), and methyl dichloroacetate (13.3 g, 93.2 mmol) were combined in dry methanol (100 mL). The solution was heated to reflux overnight. The reaction was cooled to room temperature, acidified by addition of concentrated hydrochloric acid and then reduced in volume under vacuum to about 50 mL. Water was added and the mixture was extracted with diethyl ether (3×100 mL). The combined organic solution was dried with MgSO$_4$, concentrated to a brown solid, and chromatographed (2% ethyl acetate in hexane) to yield benzo[1,3]dioxole-2-carboxylic acid methyl ester as a colorless oil.

MS (ESI): 195.10 (M+H$^+$).

$^1$H NMR (300 MHz, CDCl$_3$), δ: 6.89 (broad, 4H), 6.29 (s, 1H), 4.34 (q, J=7 Hz, 2H), 1.33 (t, J=7 Hz, 3H).

To benzo[1,3]dioxole-2-carboxylic acid methyl ester (7.21 g, 40.0 mmol) was added ammonium hydroxide (29% in water, 10 mL) and enough acetonitrile to make the mixture homogeneous (~5 mL). The solution was stirred for two hours at room temperature and then distilled water was added.

Benzo[1,3]dioxole-2-carboxylic acid amide precipitated as a white solid and was collected by filtration and used without further purification.

MS (ESI): 160.00 (M+H$^+$)

$^1$H NMR (300 MHz, DMSO), δ: 7.99 (s, broad, 1H), 7.72 (s, broad, 1H), 6.94 (m, 2H) 6.86 (m, 2H), 6.30 (s, 1H).

Benzo[1,3]dioxole-2-carboxylic acid amide (5.44 g, 32.9 mmol) was dissolved in tetrahydrofuran (THF, 100 mL). Lithium aluminum hydride (LAH, 1M in THF, 39.5 mL, 39.5 mmol) was added slowly to the solution at room temperature. The reaction was stirred at room temperature for 24 hours. Distilled water was added to destroy the excess LAH. Aqueous sodium hydroxide (3.0 M, 100 mL) was added and the solution was extracted with ethyl acetate (3×100 mL). The combined organic solution was washed with water and dried over MgSO$_4$. The solvent was evaporated to yield C-benzo[1,3]dioxol-2-yl-methylamine as a colorless oil.

MS (ESI): 152.1 (M+H$^+$)

$^1$H NMR (300 MHz, CDCl$_3$), δ: 6.87 (m, 4H), 6.09 (t, J=4 Hz, 1H), 3.13 (d, J=4 Hz, 2H)

C-Benzo[1,3]dioxol-2-yl-methylamine (2.94 g, 19.4 mmol) and sulfamide (3.74 g, 38.9 mmol) were combined in dry dioxane (50 mL) and the solution was heated to reflux overnight. The reaction was concentrated and the residue was chromatographed (2% to 10% acetone in dichloromethane) to yield the title compound as a white solid.

MS (ESI): 230.0 (M+H$^+$)

$^1$H NMR (300 MHz, CDCl$_3$), δ: 6.87 (m, 4H), 6.25 (t, J=4 Hz, 1H), 4.79 (broad, 1H), 4.62 (broad, 1H), 3.64 (d, J=4 Hz, 2H).

EXAMPLE 4

(2S)-(−)-N-(2,3-Dihydro-benzo[1,4]dioxin-2-ylmethyl)-sulfamide (Compound #4)

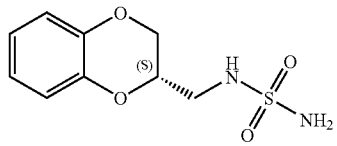

Catechol (13.2 g, 0.12 mol) and potassium carbonate (16.6 g, 0.12 mol) were stirred in DMF (250 mL) and (2R)-glycidyl tosylate (22.8 g, 0.10 mol) was added and the reaction was stirred at 60° C. for 24 h. The reaction was cooled to room temperature and diluted with ice water (1 L) and extracted with diethyl ether (4 times). The combined organic solution was washed 3 times with 10% potassium carbonate, once with water, once with brine and evaporated in vacuo to yield a white solid which was purified by flash column chromatography (DCM:Methanol—50:1) to yield ((2S)-2,3-dihydro-benzo[1,4]dioxin-2-yl)-methanol as a solid.

The solid (13.3 g, 68 mmol) was dissolved in pyridine (85 mL) cooled to 0° C., p-toluenesulfonyl chloride (13.0 g, 68 mmol) was added and the reaction mixture stirred at room temperature for 20 h. The reaction was diluted with diethyl ether (1 L) and 1N HCl (1.2 L). The organic layer was separated and washed 2 times with 1N HCl (500 mL), 4 times with water (150 mL), once with brine, dried (MgSO$_4$) and evaporated in vacuo to yield a white solid which was purified by flash column chromatography (Hept:EA—2:1) to yield toluene-4-sulfonic acid (2S)-2,3-dihydro-benzo[1,4]dioxin-2-yl-methyl ester as a white solid.

The white solid was combined with potassium phthalimide (14.4 g, 78 mmol) in DMF (250 mL) and heated to reflux for 1 h, cooled to room temperature and poured into vigorously stirring water (1.5 L) and stirred 30 min. White solid was filtered and the solid was washed several times with water, 2% NaOH, and water again and let air dry to yield a (2S)-2-(2,3-Dihydro-benzo[1,4]dioxin-2-ylmethyl)-isoindole-1,3-dione as white powdery solid.

The powdery white solid was combined with hydrazine (2.75 g, 86 mmol) in EtOH (225 mL) and heated at reflux for 2 h, cooled to room temperature and 1N HCl added to pH 1.0 and stirred for 15 min. White solid was filtered and washed with fresh EtOH (solid discarded) and the filtrate was evaporated in vacuo to a solid, which was partitioned between diethyl ether and dilute aqueous NaOH. The diethyl ether solution was dried (Na$_2$SO$_4$) and evaporated in vacuo to a yield a light yellow oil. The oil was purified by flash column chromatography (DCM:MeOH—10:1) to yield an oil. A portion of the oil (4.82 g, 29 mmol) in 2-propanol (250 mL) was treated with 1N HCl (30 mL) and heated on steambath until homogeneous and then let cool to room temperature. After 3 h, the mixture was ice cooled for 2 h. A white flaky solid (the corresponding HCl salt of (2S)—C-(2,3-Dihydro-benzo[1,4]dioxin-2-yl)-methylamine) was filtered off and then recrystallized again from 2-propanol to yield a white solid.

$[α]_D$=−69.6 (c=1.06, EtOH)

The white solid was partitioned between DCM and dilute NaOH, and the DCM was dried (NaSO$_4$) and evaporated in vacuo to yield (2S)—C-(2,3-Dihydro-benzo[1,4]dioxin-2-yl)-methylamine as an oil.

$[α]_D$=−57.8 (c=1.40, CHCl$_3$)

The oil (2.1 g, 12.7 mmol) and sulfamide (2.44 g, 25.4 mmol) were refluxed in dioxane (75 mL) for 2 h and the crude product was purified by flash column chromatography (DCM:MeOH 10:1) to yield a white solid, which was recrystallized from DCM to yield the title compound as a white crystalline solid.

mp 102-103° C.

$[α]_D$=−45.1° (c=1.05, M);

$^1$H NMR (DMSOd6) δ 6.86 (m, 4H), 6.81 (bd s, 3H, NH), 4.3 (m, 2H), 3.97 (dd, J=6.9, 11.4 Hz, 1H), 3.20 (dd, J=5.5, 13.7 Hz, 1H), 3.10 (dd, J=6.9, 13.7 Hz, 1H)

Anal Calc: C, 44.25; H, 4.95; N, 11.47; S, 13.13

Anal Found: C, 44.20; H, 4.69; N, 11.40; S, 13.22.

EXAMPLE 5

N-(2,3-Dihydro-benzo[1,4]dioxin-2-ylmethyl)-N',N' dimethylsulfamide (Compound #6)

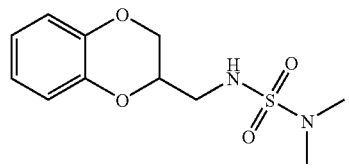

Racemic 2,3-dihydro-1,4-benzdioxin-2-ylmethylamine (8.25 g, 5.0 mmol) and triethylamine (1.52 g, 15 mmol) were combined in DMF (10 mL) and cooled in an ice bath as dimethylsulfamoyl chloride (1.44 g, 10 mmol) was added. The reaction mixture was then stirred for 3 hr with continued cooling. The reaction mixture was partitioned between ethyl acetate and water, and the ethyl acetate solution was washed with brine, dried (MgSO$_4$) and evaporated in vacuo to yield an oil. The oil was purified using flash column chromatography (ethyl acetate:Heptane—1:1) to yield a white solid, which was recrystallized (ethyl acetate/Hexane) to yield the title compound as a white floccular solid.

mp 76-78° C.

MS 273 (MH$^+$)

Anal Calc: C, 48.52; H, 5.92; N, 10.29; S, 11.78

Anal Found: C, 48.63; H, 5.62; N, 10.20; S, 11.90

$^1$H NMR (CDCl$_3$) δ 6.87 (m, 4H), 4.59 (bd m, 1H, NH), 4.35 (m, 1H), 4.27 (dd, J=2.3, 11.4 Hz, 1H), 4.04 (dd, J=7.0, 11.4, 1H), 3.36 (m, 2H), 2.82 (s, 6H).

EXAMPLE 6

N-(2,3-Dihydro-benzo[1,4]dioxin-2-ylmethyl)-N-methylsulfamide (Compound #7)

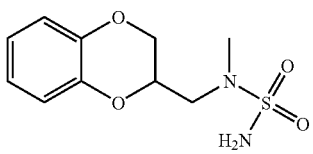

Racemic 2,3-dihydro-1,4-benzdioxin-2-ylmethylamine (825 mg, 5 mmol) was dissolved in ethyl formate (15 mL), refluxed for 30 min and evaporated in vacuo to yield N-(2,3-dihydro-benzo[1,4]dioxin-2-ylmethyl)-formamide as an oil.

The oil in diethyl ether (25 mL) was treated with 1M LAH in THF (9.0 mL, 9.0 mmol) at 0° C. and stirred for 5 h at room temperature. The reaction was cooled in an ice bath and quenched with water (0.50 mL), followed by 3 N NaOH (0.50 mL) and water (0.50 mL). The mixture was then stirred at room temperature for 1 h. Solid was filtered and the filtrate was evaporated in vacuo to yield a residue which was partitioned between 1N HCl and diethyl ether. The aqueous phase was basified with 1N NaOH and extracted with diethyl ether. The organic phase was dried (MgSO$_4$) and evaporated in vacuo to yield (2,3-dihydro-benzo[1,4]dioxin-2-ylmethyl)-methyl-amine as an oil.

MS 180 (MH$^+$)

$^1$H NMR (CDCl$_3$) δ 6.85 (m, 4H), 4.30 (m, 2H), 4.02 (dd, J=7.9, 11.6 Hz, 1H), 2.85 (m, 2H), 2.50 (s, 3H)

The oil (380 mg, 2.1 mmol) and sulfamide (820 mg, 8.5 mmol) were combined in dioxane (15 mL), refluxed for 1.5 h and evaporated in vacuo to yield a crude residue. The residue was purified via column chromatography (ethyl acetate/Heptane 1:1) and the resultant solid was recrystallized from ethyl acetate/Hexane to yield the title compound as a white solid.

mp 97-98° C.

MS 257 (M$^{-1}$)

Anal Calc: C, 46.50; H, 5.46; N, 10.85; S, 12.41

Anal Found: C, 46.48; H, 5.65; N, 10.90; S, 12.07

$^1$H NMR (CDCl$_3$) δ 6.86 (m, 4H), 4.52 (bs, 2H), 4.46 (m, 1H), 4.29 (dd, J=2.3, 11.5 Hz, 1H), 4.05 (dd, J=6.5, 11.5 Hz, 1H), 3.51 (dd, J=6.7, 14.9 Hz, 1H), 3.40 (dd, J=5.9, 14.9 Hz, 1H), 2.99 (s, 3H).

EXAMPLE 7

(2S)-(−)-N-(6-Chloro-2,3-dihydro-benzo[1,4]dioxin-2-ylmethyl)-sulfamide (Compound #8)

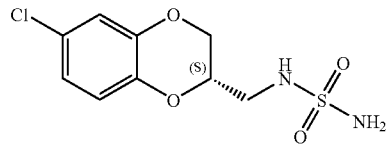

Following the procedure outlined in Example 4 above, 4-chlorocatechol was reacted to yield a mixture of (2S)—C-(7-Chloro-2,3-dihydro-benzo[1,4]dioxin-2-yl)-methylamine and (2S)—C-(6-Chloro-2,3-dihydro-benzo[1,4]dioxin-2-yl)-methylamine (ca. 3:1 ratio of 6-chloro:7-chloro isomers by RP HPLC).

The mixture was dissolved in 2-propanol (100 mL) and 1N HCl in diethyl ether was added until pH=1.0 was attained. The hydrochloride salt that precipitated was filtered (2.65 g) and re-crystallized from methanol/IPA to yield white crystals. The white crystals were partitioned between DCM and dilute NaOH. The DCM was dried and evaporated in vacuo to yield purified (2S)—C-(6-Chloro-2,3-dihydro-benzo[1,4]dioxin-2-yl)-methylamine as an oil.

$[α]_D$=−67.8 (c=1.51, CHCl$_3$)

The oil (7.75 mmol) and sulfamide (1.50 g, 15.5 mmol) were combined in dioxane (50 mL) and refluxed for 2.0 h, cooled to room temperature and evaporated in vacuo to yield a solid. The product was purified via flash column using DCM/methanol 20:1 to yield the title compound as a white solid.

MS 277 (M$^{-1}$)

$[α]_D$=−59.9° (c=1.11, M)

$^1$H NMR (CDCl$_3$) δ 6.90 (d, J=2.2 Hz, 1H), 6.81 (m, 2H), 4.76 (m, 1H), 4.55 (s, 2H), 4.40 (m, 1H), 4.29 (dd, J=2.4, 11.5Hz, 1H), 4.05 (dd, J=7.1, 11.5 Hz, 1H), 3.45 (m, 2H)

Anal Calc: C, 38.78; H, 3.98; N, 10.05

Anal Found: C, 38.80; H, 3.67; N, 9.99.

The filtrates of the crystallized hydrochloride salt of (2S)—C-(6-Chloro-2,3-dihydro-benzo[1,4]dioxin-2-yl)-methylamine prepared above were recovered (ca. 1:1 of 6-chloro:7-chloro isomers) and evaporated in vacuo to yield a solid, which was partitioned between DCM (200 mL) and dilute NaOH (0.5 M, 50 mL). The DCM solution was washed once with brine, dried (Na$_2$SO$_4$) and evaporated in vacuo to yield an oil, which was purified via reverse phase HPLC (10-50% ACN with 0.16% TFA in water with 0.20% TFA) to yield (2S)—C-(7-Chloro-2,3-dihydro-benzo[1,4]dioxin-2-yl)-methylamine as a residue.

The residue was combined with sulfamide (0.90 g, 9.4 mmol) in dioxane (25 mL) and refluxed for 2.5 h, cooled to room temperature and evaporated in vacuo to yield an oil. The oil was purified by flash column chromatography using DCM/methanol—10:1 to yield (2S)-(−)-N-(7-Chloro-2,3-dihydro-benzo[1,4]dioxin-2-ylmethyl)-sulfamide as a white solid.

MS 277 (M$^{-1}$)

¹H NMR (CDCl₃/CD₃OD) δ 6.88 (d, J=0.7 Hz, 1H), 6.81 (m, 2H), 4.37 (m, 1H), 4.30 (dd, J=2.3, 11.6 Hz, 1H), 4.04 (dd, J=7.0, 11.6 Hz, 1H), 3.38 (m, 2H).

EXAMPLE 8

Chroman-2-ylmethylsulfamide (Compound #10)

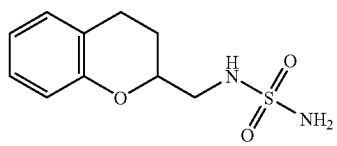

Chroman-2-carboxylic acid (4.5 g, 25 mmol) and HOBT (3.86 g, 25 mmol) were combined in DCM (40 mL) and DMF (10 mL). Dimethylaminopropyl ethylcarbodiimide (EDC, 4.84 g, 25 mmol) was added at room temperature and the reaction mixture was stirred for 30 min. Ammonium hydroxide (2.26 mL, 33.4 mmol) was added and the reaction mixture was stirred for 16 h. The reaction mixture was diluted with DCM (50 mL) and water (50 mL) and the pH of the mixture was adjusted to about pH=3.0 with 1N HCl. The DCM was separated and the aqueous phase extracted twice with DCM. The combined DCM phase was dried (Na₂SO₄) and evaporated in vacuo to yield an oil, which was purified with flash column chromatography (ethyl acetate) to yield an oil.

The oil (5.35 g, 30 mmol) in THF (90 mL) was stirred as 1M LAH in THF (36 mL, 36 mmol) was added and the reaction mixture was then stirred at room temperature for 20 h. The reaction was quenched with water, stirred for 2 hours, the solution decanted, dried (Na₂SO₄) and evaporated in vacuo to yield C-chroman-2-yl-methylamine as an oily amine.

The oily amine (1.63 g, 10 mmol) and sulfamide (1.92 g, 20 mmol) were combined in dioxane (50 mL) and brought to reflux for 2 h. The solution was cooled and evaporated in vacuo to yield an oil, which was purified via column chromatography (DCM:Methanol 10:1) to yield a white solid. The solid was recrystallized from ethyl acetate/hexane to yield chroman-2-ylmethylsulfamide as a white solid.

mp 100-101° C.
MS 241 (M⁻¹)
Anal Calc: C, 49.57; H, 5.82; N, 11.56; S, 13.23
Anal Found: C, 49.57; H, 5.80; N, 11.75; S, 13.33.

EXAMPLE 9

Chroman-2-ylmethylsulfamate (Compound #11)

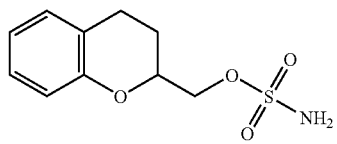

Chroman-2-carboxylic acid (4.3 g, 24 mmol) in THF (70 mL) was combined with 1M LAH in THF (30 mL, 30 mmol) and stirred at room temperature for 2 h. The reaction mixture was quenched with water and then stirred for 2 hours. The THF solution was decanted from the solid, which was washed with fresh THF. The combined THF solution was dried (Na₂SO₄) and evaporated in vacuo to yield chroman-2-yl-methanol as an oil.

The chroman-2-yl-methanol (1.97 g, 12 mmol) in DMF (30 mL) was cooled with an ice bath to about 0° C. under argon and combined with 95% NaH (0.39 g, 15.6 mmol), then stirred for 30 min. Sulfamoyl chloride (2.78 g, 24 mmol) was then added and the reaction mixture was stirred for 1 h. The reaction mixture was diluted with ethyl acetate (100 mL) and water (100 mL). The ethyl acetate solution was separated and the aqueous phase was extracted twice with ethyl acetate. The combined ethyl acetate phase was dried (MgSO₄) and evaporated in vacuo to yield an oil, which was purified by flash column chromatography (ethyl acetate/hexane 1:2) to yield a white solid, which was recrystallized from ethyl acetate/hexane to yield the title compound as a white solid.

mp 87-90° C.
MS [M-H]⁻ 242.1
Anal Calc: C, 49.37; H, 5.39; N, 5.76; S, 13.18
Anal Found: C, 49.46; H, 5.17; N, 5.72; S, 13.09.

EXAMPLE 10

2-(2,3-Dihydro-benzo[1,4]dioxin-2-yl)-ethylsulfamide (Compound #16)

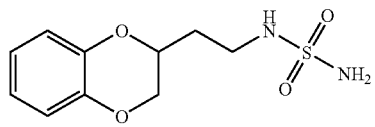

Potassium cyanide (2.05 g, 31.5 mmol) was added to 2-bromomethyl-(2,3 dihydrobenzo[1,4]dioxine) (6.87 g, 30 mmol) in DMSO (90 mL) and stirred at ambient temperature for 20 h. The reaction mixture was then diluted with water (250 mL) and extracted twice with diethyl ether. The diethyl ether was washed with water, then washed twice with brine, dried (Na₂SO₄) and evaporated in vacuo to yield 2-cyanomethyl-(2,3 dihydrobenzo[1,4]dioxine) as a white solid.

¹H NMR (CDCl₃) δ 6.89 (m, 4H), 4.50 (m, 1H), 4.31 (dd, J=2.3, 11.5 Hz, 1H), 4.08 (dd, J=6.2, 11.6 Hz, 1H), 2.78 (d, J=6.1, Hz, 2H)

The 2-cyanomethyl-(2,3 dihydrobenzo[1,4]dioxine) was dissolved in THF (50 mL) and 1M BH₃ in THF (80 mL, 80 mmol) was added and the reaction mixture refluxed for 5 h, then stirred at ambient temperature for 16 h. With ice bath cooling, 2N HCl was added until pH=1.0 was achieved. The reaction mixture was then stirred for 1 h at room temperature and evaporated in vacuo to yield an oil. The oil was partitioned between 3N NaOH and diethyl ether, and the diethyl ether solution was washed with brine, dried (Na₂SO₄) and evaporated in vacuo to yield crude 2-(2,3 dihydrobenzo[1,4]dioxin-2-yl)ethylamine.

MS (M+H)⁺180.

The crude 2-(2,3 dihydrobenzo[1,4]dioxin-2-yl)ethylamine in dioxane (100 mL) was combined with sulfamide (3.0 g, 31 mmol) and heated to reflux for 2 h. The solution was cooled and evaporated in vacuo to yield an orange solid, which was purified by column chromatography (DCM:MeOH—10:1) to yield a white solid. The solid was re-crystallized from DCM to yield the title compound as a solid.

MS (M-1) 257
MP 101-103° C. (corr)

¹H NMR (CDCl₃): δ 6.86 (m, 4H), 4.70 (m, 1H), 4.52 (s, 2H), 4.30 (m, 2H), 3.94 (dd, J=7.4, 11.3 Hz, 1H), 3.43 (dd, J=6.4, 12.9 Hz, 2H), 1.94 (dd, J=6.5, 12.9, 2H).
Elemental Analysis:
  Measured: C, 46.48; H, 5.60; N, 10.81; S, 12.41
  Calculated: C, 46.50; H, 5.46; N, 10.85; S, 12.41

EXAMPLE 11

(2S)-(−)-N-(6,7 Dichloro-2,3-dihydro-benzo[1,4] dioxin-2-ylmethyl)-sulfamide (Compound #29)

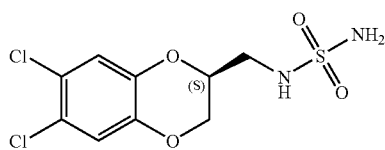

4,5 Dichloroatechol (8.6 g, 48 mmol) and potassium carbonate (6.64 g, 48 mmol) were stirred in DMF (200 mL). (2R)-Glycidyl tosylate (9.12 g, 40 mmol) was added and the reaction mixture was stirred at 60° C. for 24 h. The reaction mixture was cooled to room temperature and then diluted with ice water (600 mL) and extracted with diethyl ether (4 times). The combined organic solution was washed 3 times with 10% potassium carbonate, twice with brine, dried (MgSO₄) and evaporated in vacuo to yield a viscous oil of (2S)-2-(6,7-dichloro-2,3-dihydro-benzo[1,4]dioxine)methanol.

The (2S)-2-(6,7 dichloro-2,3-dihydro-benzo[1,4]dioxine)methanol oil (6.4 g, 27 mmol) was dissolved in pyridine (50 mL) cooled to 0° C. Then, p-toluenesulfonyl chloride (5.2 g, 27 mmol) was added and the reaction mixture was stirred at room temperature for 20 h. The reaction mixture was diluted with diethyl ether and 1N HCl (750 mL) and the organic layer was separated and washed 2 times with 1N HCl (250 mL), once with water (150 mL), twice with brine, dried (MgSO₄) and evaporated in vacuo to yield light yellow solid of toluene-4-sulfonic acid (2S)-6,7-dichloro-2,3-dihydro-benzo[1,4]dioxin-2-ylmethyl ester.
¹H NMR (CDCl3): δ 7.79 (d, J=8.3 Hz, 2H), 7.36 (d, J=8.0 Hz, 2H), 6.94 (s, 1H), 6.83 (s, 1H), 4.37 (m, 1H), 4.2 (m, 3H), 4.03 (dd, J=6.3, 11.7 Hz, 1H 2.47 (s, 3H).

Toluene-4-sulfonic acid (2S)-6,7-dichloro-2,3-dihydro-benzo[1,4]dioxin-2-ylmethyl ester (8.0 g, 20.5 mmol) was combined with potassium phthalimide (6.1 g, 33 mmol) in DMF (75 mL) and heated to reflux for 1 h, cooled to room temperature and poured into vigorously stirring water (0.5 L) and then stirred 30 min. White solid was filtered and the solid was washed several times with water, 2% NaOH, and water again and then let air dry to yield (2S)-2-(6,7-dichloro-2,3-dihydro-benzo[1,4]dioxin-2-ylmethyl)-isoindole-1,3-dione (6.0 g, 80%) as a white powdery solid.

The white powdery solid was combined with hydrazine (1.06 g, 33 mmol) in EtOH (80 mL) and heated at reflux for 2 h, then cooled to room temperature. 1N HCl was added to adjust the reaction mixture's pH to pH 1.0 and the reaction mixture was then stirred for 15 min. White solid was filtered and washed with fresh EtOH (solid discarded) and the filtrate was evaporated in vacuo to a solid, which was partitioned between diethyl ether and dilute aqueous NaOH. The diethyl ether solution was dried (Na₂SO₄) and evaporated in vacuo to a yield a viscous oil of (2S)-2-aminomethyl-(6,7-dichloro-2, 3-dihydro-benzo[1,4]dioxine).

¹H NMR (CDCl3): δ 6.98 (s, 1H), 6.96 (s, 1H), 4.25 (dd, J=2.0, 11.2 Hz, 1H), 4.15 (m, 1H), 4.0 (m, 1H), 2.97 (d, J=5.5 Hz, 2H)

A portion of the oil (3.8 g, 16 mmol) and sulfamide (3.1 g, 32.4 mmol) were refluxed in dioxane (100 mL) for 2 h and the crude product was purified by flash column chromatography (DCM:MeOH 20:1) to yield the title compound as a white solid, which was recrystallized from ethyl acetate/hexane to yield the title compound as a white crystalline solid.
MS [M−H]⁻ 311.0
mp 119-121° C.
[α]$_D$=−53.4° (c=1.17, M)
¹H NMR (DMSOd6): δ 7.22 (s, 1H), 7.20 (s, 1H), 6.91 (bd s, 1H), 6.68 (bd s, 2H), 4.35 (m, 2H), 4.05 (dd, J=6.5, 11.5 Hz, 1H), 3.15 (m, 2H)
Elemental Analysis:
  Measure: C, 34.52; H, 3.22; N, 8.95; Cl, 22.64; S, 10.24
  Calculated: C, 34.64; H, 2.68; N, 8.87; Cl, 22.94; S, 10.35.

EXAMPLE 12

(2S)-(−)-N-(7-Amino-2,3-dihydro-benzo[1,4]dioxin-2-ylmethyl)-sulfamide (Compound #36)

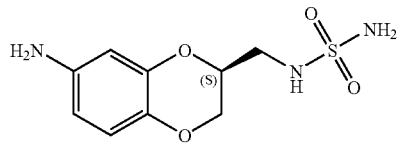

(2S )-(−)-N-(2,3-Dihydro-7-nitro-benzo[1,4]dioxin-2-yl-methyl)-sulfamide (1.2 g, 4.15 mmol), was prepared from 4-nitrocatechol according to the process outlined in Example 4. The (2S)-(−)-N-(2,3-Dihydro-7-nitro-benzo[1,4]dioxin-2-ylmethyl)-sulfamide, was then combined with 10% Pd/C in methanol (120 mL) and shaken under hydrogen atmosphere (39 psi) at room temperature for 3 h. The solids were filtered and washed with 10% M in DCM and the filtrate was evaporated in vacuo to yield crude product. The crude product was dissolved in 0.2 N HCl (25 mL), frozen and lyophilized to yield the title compound as a white flaky solid, as the corresponding hydrochloride salt.
MS (M+H)⁺260
¹H NMR (DMSO d6): δ 10.2 (bd s, 3H), 6.86 (m, 1H), 6.85 (s, 1H), 6.74 (dd, J=2.5, 8.4 Hz, 1H), 4.22 (m, 2H), 3.88 (dd, J=6.7, 11.4 Hz, 1H), 3.04 (m, 2H)

EXAMPLE 13

(2S)-(−)-N-(7-Methyl-2,3-dihydro-benzo[1,4]dioxin-2-ylmethyl)-sulfamide (Compound #19)

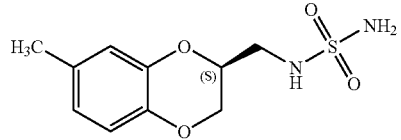

Title compound was prepared according to the procedure described in Example 4 above, starting with 4-methylcatechol, to yield a white solid, which was recrystallized from ethyl acetate/hexane to yield the title compound as a white solid.

MS [M−H]⁻ 257

¹H NMR (CDCl3): δ 6.76 (m, 1H), 6.66 (m, 2H), 4.80 (m, 1H), 4.57 (bd s, 1H), 4.40 (m, 1H), 4.28 (m, 1H), 4.03 (dd, J=6.9, 11.4 Hz, 1H), 3.45 (m, 2H), 2.25 (s, 3H).

Elemental Analysis

Calculated: C, 46.50; H, 5.46; N, 10.85; S, 12.41
Found: C, 46.65; H, 5.60; N, 10.84; S, 12.61.

EXAMPLE 14

Sulfamic acid, 6.7 dichloro-2,3-dihydro-benzo[1,4]dioxin-2-ylmethyl ester (Compound #27)

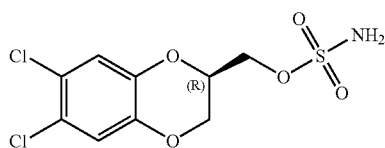

(2S)-6,7 dichloro-2,3-dihydro-benzo[1,4]dioxin-2-ylmethanol (2.0 g, 8.5 mmol), prepared according to the procedure described in Example 11 above, in DMF (20 mL) was cooled in an ice bath. Then, 95% sodium hydride (0.28 g, 11 mmol) was added under argon and the reaction mixture was stirred 30 min. Sulfamoyl chloride (1.97 g, 17 mmol) was added and the reaction mixture was stirred with ice bath cooling. After 1 h, the reaction mixture was diluted with water (50 mL) and extracted three times with ethyl acetate. The combined ethyl acetate was washed with brine, dried (Na₂SO₄) and evaporated in vacuo to an oil, which was purified by flash column chromatography (ethyl acetate/heptane 1:1) to yield a white solid. The white solid was recrystallized from benzene to yield the title compound as a white solid.

mp 109-111° C.

MS [M−H]⁻ 312

¹H NMR (DMSOd6) δ 7.65 (s, 2H), 7.26 (s, 1H), 7.25 (s, 1H), 4.58 (m, 1H), 4.41 (dd, J=2.5, 11.7Hz, 1H), 4.28 (m, 2H), 4.11 (dd, J=6.9, 11.7Hz, 1H).

EXAMPLE 15

Sulfamic acid, 6-chloro-2,3-dihydro-benzo[1,4]dioxin-2-ylmethyl ester (Compound #12)

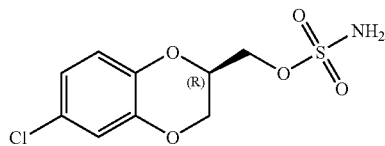

(2S)-6-Chloro-2,3-dihydro-benzo[1,4]dioxin-2-ylmethanol (6.4 g, 32 mmol) was prepared according to procedure as in Example 7 above, in DMF (80 mL) was cooled in an ice bath. Then, 95% sodium hydride (1.06 g, 42 mmol) was added over 20 min under argon and the reaction mixture was stirred 30 min. Sulfamoyl chloride (7.4 g, 64 mmol) was added over 10 min and the reaction mixture was stirred with ice bath cooling. After 1 h, the reaction was diluted with water (300 mL) and extracted three times with ethyl acetate. The combined ethyl acetate was washed with brine, dried (MgSO₄) and evaporated in vacuo to yield an oil, which was purified by flash column chromatography (ethyl acetate/hexane 1:2) to yield a white solid. The white solid was recrystallized from benzene 3 times to yield the title compound as a white solid.

mp 113-116° C.

MS [M−H]⁻ 278

[α]_D=−41.0° (c=1.32, M)

¹H NMR (CDCl3) δ 6.91 (d, J=1.9 Hz, 1H), 6.84 (m, 2H), 4.82 (bd s, 2H), 4.50 (m, 1H), 4.41 (m, 2H), 4.31 (dd, J=2.3, 11.6 Hz, 1H), 4.12 (dd, J=6.3, 11.6 Hz, 1H)

Elemental Analysis:

Measured: C, 38.57; H, 3.42; N, 4.92; S, 11.53
Calculated: C, 38.65; H, 3.60; N, 5.01; S, 11.46

EXAMPLE 16

In Vivo Assay: Maximal Electroshock Test (MES)

Anticonvulsant activity was determined using the MES test, run according to the procedure described in detail below. Swinyard E A, Woodhead J H, White H S, Franklin M R. Experimental selection, quantification, and evaluation of anticonvulsants. In Levy R H, et al., eds. *Antiepileptic Drugs*. 3rd ed. New York: Raven Press, 1989:85-102

CF-1 male albino mice (25-35 g) were fasted for 16 hours before testing. Mice were randomly selected into control and test groups, with the animals dosed with vehicle or test compound, at varying concentrations, respectively. On the study date, at 30 minutes prior to shock, the mice were orally dosed with vehicle (0.5% methylcellulose) or test compound (100-300 mg/kg). Seizures were induced by trans-corneal electric shock using a 60-Hz alternating current, 50 mA, delivered for 0.2 sec. The mice in the test groups were subjected to electrical stimulus at time intervals between 15 minutes and 4 hours following administration of test compound. The shock resulted in an immediate full body tonic extension. The test was complete when the entire course of the convulsion has been observed (typically, less than 1 minute after electrical stimulation), and the mice were then immediately euthanized by carbon dioxide inhalation.

Abolition of the full body tonic extensor component of the seizure was taken as the endpoint of the test. Absence of this component indicated that the test compound had the ability to prevent the spread of seizure discharge through neural tissue. The $ED_{50}$ value of the test compound (calculated when appropriate) was the calculated dose required to block the hind limb tonic-extensor component of the MES-induced seizure in 50% of the rodents tested. A probit analysis was used to calculate the $ED_{50}$ and 95% fiducial limits (FL).

Representative compounds of the present invention were tested according to the procedure described above, with results as listed in Table 4 below. Results are listed as number of mice with full body tonic extension prevented/total number of mice tested @ time (at a given test compound dosage level).

TABLE 4

MES Mouse Activity

| ID No. | MES Activity |
|---|---|
| 1 | 2/4 @ 1 h (300 mg/kg) |
| 2 | 4/4 @ 2 h (100 mg/kg) |
| 3 | 2/3 @ 1 h (300 mg/kg) |
| 4 | 5/5 @ 1 h (300 mg/kg) |
| 5 | 1/5 @ 2 h (300 mg/kg) |
| 6 | 4/5 @ 0.5 h (300 mg/kg) |
| 7 | 3/3 @ 0.5 h (300 mg/kg) |
| 8 | 3/5 @ 3 h (100 mg/kg) |
| 9 | 1/5 @ 1 h (300 mg/kg) |
| 10 | 1/5 @ 1 h (100 mg/kg) |
| 11 | 4/5 @ 1 h (100 mg/kg) |
| 12 | 3/5 @ 4 h (100 mg/kg) |
| 13 | 2/5 @ 0.5 h (10 mg/kg) |
| 14 | 3/5 @ 4 h (100 mg/kg) |
| 15 | Inactive @ 100 mg/kg |
| 16 | 5/5 @ 0.5 h (300 mg/kg) |
| 17 | 4/5 @ 0.5 h (100 mg/kg) |
| 18 | Inactive @ 100 mg/kg |
| 19 | 5/5 @ 0.5 h (300 mg/kg) |
| 20 | 1/5 @ 2 h (100 mg/kg) |
| 21 | 5/5 @ 2 h (100 mg/kg) |
| 22 | 1/5 @ 4 h (100 mg/kg) |
| 23 | Inactive @ 100 and 300 mg/kg |
| 24 | 5/5 @ 4 h (300 mg/kg) |
| 25 | 5/5 @ 4 h (100 mg/kg) |
| 26 | Inactive @ 100 and 300 mg/kg |
| 27 | 5/5 @ 4 h (100 mg/kg) |
| 28 | 4/5 @ 4 h (100 mg/kg) |
| 29 | 3/5 @ 4 h (100 mg/kg) |
| 30 | 1/5 @ 0.5 h (100 mg/kg) |
| 31 | 3/5 @ 0.5 h (100 mg/kg) |
| 32 | Inactive @ 100 and 300 mg/kg |
| 33 | 1/3 @ 2 h (300 mg/kg) |
| 34 | Inactive @ 100 and 300 mg/kg |
| 35 | Inactive at 100 mg/kg |
| 36 | Inactive @ 100 and 300 mg/kg |

EXAMPLE 17

As a specific embodiment of an oral composition, 100 mg of the Compound #8 as in Example 7 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (II)

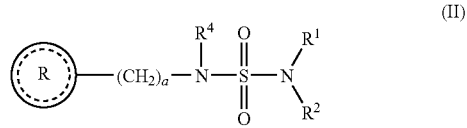

(II)

wherein $R^1$ and $R^2$ are each independently selected from the group consisting of hydrogen and lower alkyl;

$R^4$ is selected from the group consisting of hydrogen and lower alkyl;

a is an integer from 1 to 2;

is selected from the group consisting of

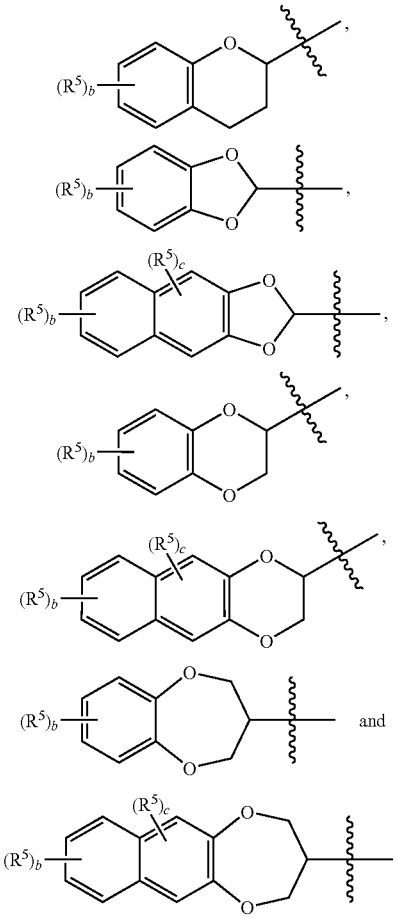

wherein b is an integer from 0 to 4; and wherein c is an integer from 0 to 2;

each $R^5$ is independently selected from the group consisting of halogen and lower alkyl;

provided that when

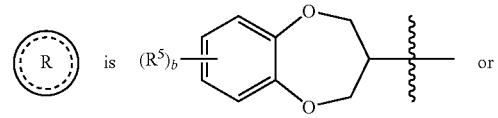

-continued

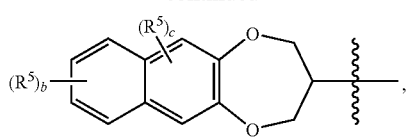

then a is 1;

or a pharmaceutically acceptable salt thereof.

2. A compound as in claim 1 wherein

R¹ and R² are each independently selected from the group consisting of hydrogen and lower alkyl;

R⁴ is selected from the group consisting of hydrogen and lower alkyl;

a is an integer from 1 to 2;

is selected from the group consisting of

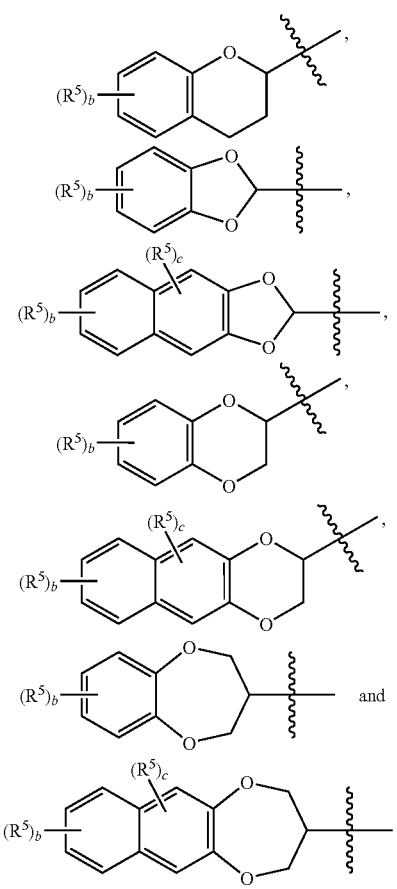

wherein b is an integer from 0 to 2; and wherein c is an integer from 0 to 1;

each $R^5$ is independently selected from the group consisting of halogen and lower alkyl;

provided that when

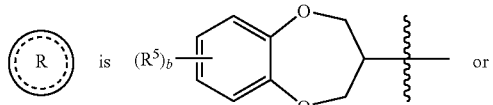

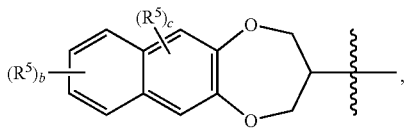

then a is 1;

or a pharmaceutically acceptable salt thereof.

3. A compound as in claim 2 wherein

R¹ and R² are each independently selected from the group consisting of hydrogen and lower alkyl;

R⁴ is selected from the group consisting of hydrogen and lower alkyl;

a is an integer from 1 to 2;

is selected from the group consisting of

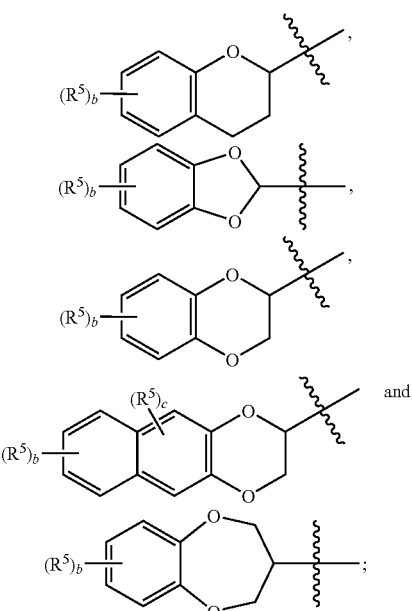

wherein b is an integer from 0 to 2; and wherein c is 0;

each $R^5$ is independently selected from the group consisting of halogen and lower alkyl;

provided that when

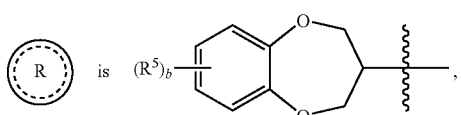

then a is 1;

or a pharmaceutically acceptable salt thereof.

4. A compound as in claim 3 wherein

R$^1$ and R$^2$ are each independently selected from the group consisting of hydrogen and lower alkyl;

R$^4$ is selected from the group consisting of hydrogen and methyl;

a is an integer from 1 to 2;

is selected from the group consisting of 2-(2,3-dihydro-benzo[1,4]dioxinyl), 2-(benzo[1,3]dioxolyl), 3-(3,4-dihydro-2H-benzo[1,4]dioxepinyl), 2-(6-chloro-2,3-dihydro-benzo[1,4]dioxinyl), 2-(6-fluoro-2,3-dihydro-benzo[1,4]dioxinyl), 2-(chromanyl), 2-(5-fluoro-2,3-dihydro-benzo[1,4]dioxinyl), 2-(7-chloro-2,3-dihydro-benzo[1,4]dioxinyl), 2-(6-chloro-benzo[1,3]dioxolyl), 2-(7-methyl-2,3-dihydro-benzo[1,4]dioxinyl), 2-(5-chloro-2,3-dihydro-benzo[1,4]dioxinyl), 2-(6-bromo-2,3-dihydro-benzo[1,4]dioxinyl), 2-(6,7-dichloro-2,3-dihydro-benzo[1,4]dioxinyl), 2-(8-chloro-2,3-dihydro-benzo[1,4]dioxinyl), 2-(2,3-dihydro-naphtho[2,3-b][1,4]dioxinyl) and 2-(4-methyl-benzo[1,3]dioxolyl);

provided that when

is 3-(3,4-dihydro-2H-benzo[1,4]dioxepinyl), then a is 1;

or a pharmaceutically acceptable salt thereof.

5. A compound as in claim 4 wherein

R$^1$ and R$^2$ are each independently selected from the group consisting of hydrogen and methyl;

R$^4$ is selected from the group consisting of hydrogen and methyl;

a is an integer from 1 to 2;

is selected from the group consisting of 2-(benzo[1,3]dioxolyl), 2-(2,3-dihydro-benzo[1,4]dioxinyl), 2-(6-chloro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(6-bromo-2,3-dihydro-benzo[1,4]dioxinyl) and 2-(6,7-dichloro-2,3-dihydro-benzo[1,4]dioxinyl);

or a pharmaceutically acceptable salt thereof.

6. A compound selected from the group consisting of N-[(6-chloro-2,3-dihydro-1,4-benzodioxin-2-yl)methyl]-sulfamide and pharmaceutically acceptable salts thereof.

7. A compound selected from the group consisting of

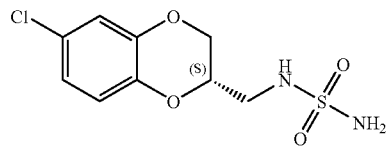

and pharmaceutically acceptable salts thereof.

8. A compound of the formula (III)

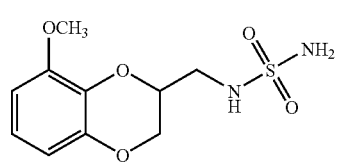

or a pharmaceutically acceptable salt thereof.

9. A pharmaceutical composition comprising a pharmaceutically acceptable carrier and a compound of claim 1.

10. A pharmaceutical composition made by mixing a compound of claim 1 and a pharmaceutically acceptable carrier.

11. A process for making a pharmaceutical composition comprising mixing a compound of claim 1 and a pharmaceutically acceptable carrier.

12. A method of treating epilepsy or a related disorder, in a subject in need thereof comprising administering to the subject a therapeutically effective amount of the compound of claim 1.

13. A method of treating epilepsy, in a subject in need thereof comprising administering to the subject a therapeutically effective amount of the compound of claim 1.

14. A method as in claim 12, wherein the disorder is selected from essential tremor or restless limb syndrome.

15. A pharmaceutical composition comprising a pharmaceutically acceptable carrier and a compound of the formula:

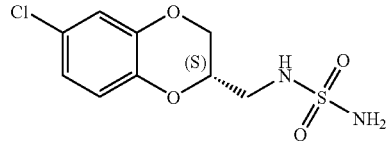

and pharmaceutically acceptable salts thereof.

16. A method of treating epilepsy or a related disorder, in a subject in need thereof comprising administering to the subject a therapeutically effective amount of the compound of the formula:

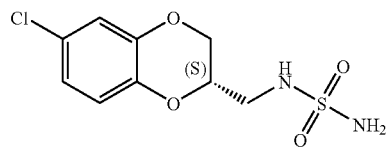

and pharmaceutically acceptable salts thereof.

17. A method of treating epilepsy, in a subject in need thereof comprising administering to the subject a therapeutically effective amount of the compound of the formula:

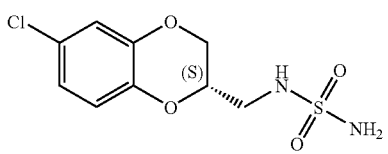

and pharmaceutically acceptable salts thereof.

18. The method of claim 17 wherein the epilepsy is selected from the group consisting of localization-related epilepsy, generalized epilepsy, epilepsy with both generalized and local seizures.

19. The method of claim 16 wherein the epilepsy or related disorder is a complication of a disease or condition selected from the group consisting of encephalopathy, phenylketonuria, juvenile Gaucher's disease, Lundborg's progressive myoclonic epilepsy, stroke, head trauma, stress, hormonal changes, drug use or withdrawal, alcohol use or withdrawal, and sleep deprivation.

20. The method of claim 16 wherein the epilepsy or related disorder is selected from essential tremor or restless limb syndrome.

* * * * *

UNITED STATES PATENT AND TRADEMARK OFFICE
CERTIFICATE OF CORRECTION

Page 1 of 1

PATENT NO.     : 8,084,490 B2
APPLICATION NO. : 11/154443
DATED          : December 27, 2011
INVENTOR(S)    : McComsey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 766 days.

Signed and Sealed this
Fifteenth Day of May, 2012

David J. Kappos
*Director of the United States Patent and Trademark Office*